United States Patent [19]

Roe et al.

[11] Patent Number: 5,124,188

[45] Date of Patent: Jun. 23, 1992

[54] POROUS, ABSORBENT, POLYMERIC MACROSTRUCTURES AND METHODS OF MAKING THE SAME

[75] Inventors: Donald C. Roe; Frank H. Lahrman; Charles J. Berg, all of Cincinnati, Ohio

[73] Assignee: The Procter & Gamble Company, Cincinnati, Ohio

[21] Appl. No.: 503,393

[22] Filed: Apr. 2, 1990

[51] Int. Cl.$^5$ .......................... B32B 3/10; B32B 5/02; B32B 3/12

[52] U.S. Cl. ...................................... 428/72; 428/76; 428/220; 428/311.5; 428/317.9; 521/919

[58] Field of Search .................. 428/76, 72, 71, 311.5, 428/220, 317.9; 521/919; 264/126

[56] References Cited

U.S. PATENT DOCUMENTS

| | | | |
|---|---|---|---|
| Re. 32,649 | 4/1988 | Brandt et al. | 604/368 |
| 3,661,154 | 5/1972 | Torr | 128/284 |
| 3,670,731 | 6/1972 | Harmon | 128/284 |
| 3,901,236 | 8/1975 | Assarsson et al. | 128/284 |
| 3,957,741 | 5/1976 | Rembaum et al. | 526/312 |
| 4,093,776 | 6/1978 | Aoki et al. | 428/402 |
| 4,127,944 | 12/1978 | Giacobello | 34/9 |
| 4,190,563 | 2/1980 | Bosley et al. | 260/17.4 GC |
| 4,282,121 | 8/1981 | Goodrich | 260/17.4 GC |
| 4,286,082 | 8/1981 | Tsubakimoto et al. | 526/240 |
| 4,410,571 | 10/1983 | Korpman | 106/162 |
| 4,413,995 | 11/1983 | Korpman et al. | 604/368 |
| 4,429,001 | 1/1984 | Kolpin et al. | 428/283 |
| 4,439,385 | 3/1984 | Kuhls et al. | 264/37 |
| 4,500,670 | 2/1985 | McKinley et al. | 524/445 |
| 4,541,871 | 9/1985 | Obayashi et al. | 106/197.2 |
| 4,551,191 | 11/1985 | Kock et al. | 156/276 |
| 4,578,068 | 3/1986 | Kramer et al. | 604/368 |
| 4,587,308 | 5/1986 | Makita et al. | 525/373 |
| 4,610,678 | 9/1986 | Weisman et al. | 604/368 |
| 4,625,001 | 11/1986 | Tsubakimoto et al. | 526/88 |
| 4,666,983 | 5/1987 | Tsubakimoto et al. | 526/88 |
| 4,673,402 | 6/1987 | Weisman et al. | 604/368 |
| 4,693,713 | 9/1987 | Chmelir et al. | 604/368 |
| 4,734,478 | 3/1988 | Tsubakimoto et al. | 527/300 |
| 4,735,987 | 4/1988 | Morita et al. | 524/436 |
| 4,758,617 | 7/1988 | Tanioku et al. | 524/436 |
| 4,766,173 | 8/1988 | Bailey et al. | 524/819 |
| 4,783,510 | 11/1988 | Saotome | 525/387 |
| 4,798,861 | 1/1989 | Johnson et al. | 524/458 |
| 4,806,598 | 2/1989 | Morman | 525/63 |
| 4,822,453 | 4/1989 | Dean et al. | 162/157.6 |
| 4,824,901 | 4/1989 | Alexander et al. | 524/555 |
| 4,826,880 | 5/1989 | Lesniak et al. | 521/53 |
| 4,833,179 | 5/1989 | Young et al. | 522/183 |
| 4,861,539 | 8/1989 | Allen et al. | 264/204 |
| 5,002,986 | 3/1991 | Fujiura et al. | 524/734 |

FOREIGN PATENT DOCUMENTS

| | | |
|---|---|---|
| 0303440A2 | 2/1989 | European Pat. Off. . |
| 0304952A2 | 3/1989 | European Pat. Off. . |
| 0312952A2 | 4/1989 | European Pat. Off. . |
| 233014A | 8/1989 | European Pat. Off. . |

(List continued on next page.)

*Primary Examiner*—Alexander S. Thomas
*Attorney, Agent, or Firm*—Steven W. Miller; Bart S. Hersko; Fredrick H. Braun

[57] ABSTRACT

Absorbent polymeric macrostructures that are porous and comprise an interparticle crosslinked aggregate having a circumscribed dry volume greater than about 10.0 mm$^3$. The interparticle crosslinked aggregrate comprises a multiplicity of precursor particles of substantially water-soluble, absorbent, hydrogel-forming, polymer material; and an interparticle crosslinking agent reacted with the polymer material of the precursor particles to form crosslink bonds between the precursor particles. Because of the particulate nature of the precursor particles, the macrostructure has pores between adjacent precursor particles. The pores are interconnected by intercommunicating channels such that the macrostructure is liquid permeable.

30 Claims, 5 Drawing Sheets

FOREIGN PATENT DOCUMENTS

| | | |
|---|---|---|
| 0326382A2 | 8/1989 | European Pat. Off. . |
| 0349240A2 | 1/1990 | European Pat. Off. . |
| 0401044 | 6/1990 | European Pat. Off. . |
| 3741157 | 6/1989 | Fed. Rep. of Germany . |
| 3741158A1 | 6/1989 | Fed. Rep. of Germany . |
| 57-44627 | 3/1982 | Japan . |
| 60-147475 | 8/1985 | Japan . |
| 60-163956 | 8/1985 | Japan . |
| 60-177004 | 9/1985 | Japan . |
| 60-255814 | 12/1985 | Japan . |
| 61-16903 | 1/1986 | Japan . |
| 62-112654 | 5/1987 | Japan . |
| 62-223203 | 10/1987 | Japan . |
| 63-21902 | 1/1988 | Japan . |
| 63-023846 | 8/1989 | Japan . |
| 63-025935 | 8/1989 | Japan . |
| 64-289790 | 8/1989 | Japan . |
| 89-303789 | 9/1989 | Japan . |
| 63-109897 | 11/1989 | Japan . |
| HEI 2-227435 | 9/1990 | Japan . |
| 1376091 | 12/1974 | United Kingdom . |

POROUS, ABSORBENT, POLYMERIC MACROSTRUCTURES AND METHODS OF MAKING THE SAME

FIELD OF THE INVENTION

The present invention relates to absorbent polymeric compositions which, upon contacting liquids such as water or body exudates, swell and imbibe such liquids. More specifically, the present invention relates to polymeric compositions that are macrostructures such as a sheet, film, or strip. Such absorbent polymeric macrostructures are porous so as to be liquid permeable. These porous, absorbent, polymeric macrostructures are useful by themselves or in absorbent articles such as diapers, adult incontinence pads, sanitary napkins, and the like. The present invention also relates to methods of producing such porous, absorbent, polymeric macrostructures.

BACKGROUND OF THE INVENTION

Particulate, absorbent, polymeric compositions are capable of absorbing large quantities of liquids such as water and body exudates and which are further capable of retaining such absorbed liquids under moderate pressures. These absorption characteristics of such polymeric compositions make them especially useful for incorporation into absorbent articles such as diapers. For example, U.S. Pat. No. 3,699,103 issued to Harper et al. on Jun. 13, 1972 and U.S. Pat. No. 3,670,731 issued to Harmon on Jun. 20, 1972, both disclose the use of particulate, absorbent, polymeric compositions (also referred to as hydrogels, superabsorbent, or hydrocolloid materials) in absorbent articles.

Conventional particulate, absorbent, polymeric compositions, however, have the limitation that the particles are not immobilized and are free to migrate during processing and/or use. Migration of the particles during processing can lead to material handling losses during manufacturing operations as well as nonhomogeneous incorporation of the particles into structures in which the particles are being used. A more significant problem, though, occurs when these particulate materials migrate during or after swelling. Such mobility leads to high resistance to liquid flow through the material due to the lack of stable interparticle capillary or liquid transport channels. This phenomenon is one form of what is commonly referred to as "gel blocking".

One attempt to overcome the performance limitations associated with particle mobility in the context of their use in absorbent articles has been the incorporation of the particulate, absorbent, polymeric compositions into tissue laminates (layered absorbent members). By encapsulating the particles between tissue layers, the overall particle mobility within an absorbent member is diminished. However, upon liquid contact, the particles within the laminate are often free to move relative to each other resulting in the breakdown of any preexistent interparticle capillary channels.

Another attempted solution has been to immobilize the particulate, absorbent, polymeric compositions by the addition of large quantities of liquid polyhydroxy compounds that act as an adhesive to hold the particles together or to a substrate. An example of this technology is disclosed in U.S. Pat. No. 4,410,571 issued to Korpman on Oct. 18, 1983. While this approach does limit migration before and, to some extent, during swelling, the particles eventually become detached from each other upon presentation of excess liquid to such polymeric compositions, resulting again in the breakdown of any preexisting capillary channels between the particles.

A further attempt to overcome the problem has been to produce a superabsorbent film via extrusion of a solution of a linear polymer and subsequent crosslinking of the polymer. An example of this technology is disclosed in U.S. Pat. No. 4,861,539 issued to Allen et al. on Aug. 29, 1989. While these superabsorbent films may absorb significant quantities of liquids, they have limited liquid transport properties and are prone to gel blocking due to their lack of internal capillary channels.

Therefore, the present invention seeks to resolve the above problems by providing a porous, absorbent, polymeric macrostructure.

Thus, it is an object of the present invention to provide absorbent polymeric macrostructures that are porous.

It is a further object of the present invention to provide absorbent polymeric macrostructures that remain intact and transport liquid even upon saturation with excess liquid.

It is a still further object of the present invention to provide absorbent polymeric macrostructures wherein the component precursor particles and pores retain their relative geometry and spatial relationships even upon saturation with excess liquid.

It is an even further object of the present invention to provide absorbent polymeric macrostructures that increase in liquid permeability upon swelling.

It is another object of the present invention to provide a method for producing such absorbent polymeric macrostructures.

It a further object of the present invention to provide improved absorbent products, absorbent members, and absorbent articles (such as diapers or sanitary napkins) incorporating the absorbent polymeric macrostructures of the present invention.

SUMMARY OF THE INVENTION

The present invention provides an absorbent polymeric macrostructure that is porous. The porous, absorbent, polymeric macrostructure comprises an interparticle crosslinked aggregate having a circumscribed dry volume greater than about 10.0 mm$^3$. The interparticle crosslinked aggregate comprises a multiplicity of precursor particles of substantially water-insoluble, absorbent, hydrogel-forming, polymer material; and an interparticle crosslinking agent reacted with the polymer material of the precursor particles to form crosslink bonds between different precursor particles. Because of the particulate nature of the precursor particles, the macrostructure has pores between adjacent precursor particles. The pores are interconnected by intercommunicating channels such that the macrostructure is liquid permeable (i.e., has capillary transport channels).

Due to the interparticle crosslink bonds formed between the precursor particles forming the interparticle crosslinked aggregate, the resultant macrostructure has improved structural integrity, increased liquid acquisition and distribution rates, and minimal gel blocking characteristics. It has been found that when the macrostructure is contacted with liquids, the macrostructure swells generally isotropically even under moderate confining pressures, imbibes such liquids into the precursor particles, and absorbs such liquids into the pores.

The isotropic swelling of the macrostructure allows the precursor particles and the pores to maintain their relative geometry and spatial relationships even when swollen. Thus, the macrostructures are relatively "fluid stable" in that the precursor particles do not dissociate from each other, thereby minimizing the incidence of gel blocking and allowing the capillary channels to be maintained and enlarged when swollen so that the macrostructure may acquire and transport subsequent loadings of liquid, even excess liquid.

The present invention also relates to improved absorbent products, absorbent members, and absorbent articles incorporating the porous, absorbent, polymeric macrostructures of the present invention. The macrostructures enhance the liquid handling characteristics of such products by rapidly acquiring liquids, efficiently distributing and storing such liquids, allowing for the acquisition and transport of subsequent loadings of liquids, and minimizing gel blocking and gel migration within such products.

The present invention also relates to methods of producing such porous, absorbent, polymeric macrostructures. The macrostructures are produced by applying an interparticle crosslinking agent onto the precursor particles, physically associating the precursor particles into an aggregate, and reacting the interparticle crosslinking agent with the polymer material of the precursor particles to form crosslink bonds between different precursor particles. In a preferred embodiment, the macrostructures are produced by shaping the aggregate of the associated precursor particles to form macrostructures of a desired shape, size, and/or density. The component precursor particles of the macrostructures may also be surface crosslinked.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

Porous, absorbent, polymeric macrostructures of the present invention are structures capable of absorbing large quantities of liquids such as water and/or body exudates (e.g., urine or menses) and which are capable of retaining such liquids under moderate pressures. Typically, the porous, absorbent, polymeric macrostructures of the present invention will swell generally isotropically and rapidly absorb the liquids.

As used herein, the term "macrostructure" means a product having a circumscribed volume when substantially dry (i.e., circumscribed dry volume) of at least about 10.0 mm$^3$, preferably at least about 100 mm$^3$, more preferably at least about 500 mm$^3$. Typically, the macrostructures of the present invention will have a circumscribed dry volume much greater than about 500 mm$^3$. In preferred embodiments of the present invention, the macrostructures have a circumscribed dry volume of between about 1000 mm$^3$ and about 100,000 mm$^3$.

While the macrostructures of the present invention may have a number of shapes and sizes, the macrostructures are typically in the form of sheets, films, cylinders, blocks, spheres, fibers, filaments, or other shaped elements. The macrostructures will generally have a thickness or diameter between about 0.25 mm and about 10.0 mm. Preferably for use in absorbent products, the macrostructures are in the form of a sheet. The term "sheet" as used herein describes macrostructures having a thickness greater than about 250 microns. The sheets will preferably have a thickness between about 0.5 mm and about 3 mm, typically about 1 mm.

The macrostructures of the present invention are formed from polymer materials capable of absorbing large quantities of liquids. (Such polymer materials are commonly referred to as hydrogel, hydrocolloid, or superabsorbent materials.) The macrostructures preferably comprise substantially water-insoluble, absorbent, hydrogel-forming, polymer material. The specific polymer materials will be discussed herein with respect to the polymer materials forming the precursor particles.

Figure 1:
FIG. 1 is a photomicrograph enlarged approximately 40 times showing a perspective view (at 15° from the horizontal) of the edge of a porous, absorbent, polymeric macrostructure of the present invention.
Figure 3:
FIG. 3 is a photomicrograph enlarged approximately 30 times showing a perspective view (at 45° from the horizontal) of the corner of the macrostructure shown in FIG. 1.

As shown in FIGS. 1 and 3, the porous, absorbent, polymeric macrostructures of the present invention comprise an interparticle crosslinked aggregate. An interparticle crosslinked aggregate is the porous structure formed by joining together two or more, typically about ten or more in the present invention, previously independent precursor particles. The precursor particles are joined together by interparticle crosslinking agents applied thereto and subjected to conditions, while maintaining the physical association of the precursor particles, which are sufficient to react the interparticle crosslinking agent with the polymer material of the precursor particles to form crosslink bonds between the precursor particles that form the aggregate.

Figure 2:
FIG. 2 is a photomicrograph enlarged approximately 120 times of a top view of a portion of the macrostructure shown in FIG. 1.

As shown in FIG. 1, the interparticle crosslinked aggregate is formed from a multiplicity of precursor particles. Due to the preferred size for the precursor particles used herein, the interparticle crosslinked aggregate is typically formed from ten or more, preferably about fifty or more, precursor particles. The precursor particles of the present invention are in the form of discrete units. The precursor particles can comprise granules, pulverulents, spheres, flakes, fibers, aggregates or agglomerates. Thus, the precursor particles can have any desired shape such as cubic; rod-like; polyhedral; spherical; rounded; angular; irregular; randomly-sized irregular shapes (e.g., pulverulent products of a grinding or pulverizing step) or shapes having a large greatest dimension/smallest dimension ratio like needle-like, flake-like, or fibrous shapes, and the like. Preferably, as shown in FIGS. 1-3, the precursor particles are in a finely divided powder form of randomly-sized irregular shaped pulverulent granules or flakes.

Although the precursor particles may have a size varying over a wide range, specific particle size distributions and sizes are preferred. For purposes of the present invention, particle size is defined for precursor particles that do not have a large greatest dimension/smallest dimension ratio such as fibers (e.g., granules, flakes, or pulverulents) as the dimension of a precursor particle which is determined by sieve size analysis. Thus, for example, a precursor particle that is retained on a standard #30 sieve with 600 micron openings is considered to have a particle size greater than 600 microns, a precursor particle that passes through the #30 sieve with 600 micron openings and is retained on a standard #35 sieve with 500 micron openings is considered to have a particle size between 500 and 600 microns, and a precursor particle that passes through a #35 sieve with 500 micron openings is considered to have a particle size less than 500 microns. In preferred embodiments of the present invention, the precursor particles will generally range in size from between about 1 micron to about 2000 microns, more preferably between about 20 microns to about 1000 microns.

Further, for purposes of this invention, the mass average particle size of the precursor particles is important in determining the characteristics and properties of the resultant macrostructures. The mass average particle size of a given sample of precursor particles is defined as the particle size which is the average particle size of the sample on a mass basis. A method for determining the mass average particle size of a sample is described hereinafter in the Test Methods section. The mass average particle size of the precursor particles will generally be from about 20 microns to about 1500 microns, more preferably from about 50 microns to about 1000 microns. In preferred embodiments of the present invention, the precursor particles have a mass average particle size less that about 1000 microns, more preferably less than about 600 microns, most preferably less than about 500 microns. In especially preferred embodiments of the present invention, the mass average particle size of the precursor particles is relatively small (i.e., the precursor particles are fines). In these embodiments, the mass average particle size of the precursor particles is less than about 300 microns, more preferably less than about 180 microns. In an exemplary embodiment, at least about 95% by weight of the precursor particles have a particle size between about 150 microns and about 300 microns. In an alternative embodiment, at least about 95% by weight of the precursor particles have a particle size between about 90 microns and about 180 microns. Narrow precursor particle size distributions are preferred because they result in a higher porosity macrostructure due to their higher void fraction when densified versus broader precursor particle size distributions with equivalent mass average particle sizes.

The particle size of materials having a large greatest dimension/smallest dimension such as fibers is typically defined by their largest dimension. For example, if absorbent, polymeric fibers (i.e., superabsorbent fibers) are used in the macrostructures of the present invention, the length of the fibers is used to define the "particle size". (The denier and/or the diameter of the fibers may also be specified.) In exemplary embodiments of the present invention, the fibers have a length greater than about 5 mm, preferably between about 10 mm and about 100 mm, more preferably between about 10 mm and about 50 mm.

The precursor particles comprise substantially water-insoluble, absorbent, hydrogel-forming, polymer material. Examples of polymer materials suitable for use as the precursor particles herein include those which are prepared from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof.

Some non-acid monomers may also be used to prepare the precursor particles herein. Such non-acid monomers can include, for example, the water-soluble or water-dispersible esters of the acid-containing monomers as well as monomers which contain no carboxyl or sulfonic acid groups at all. Optional non-acid monomers can thus include monomers containing the following types of functional groups: carboxylic acid or sulfonic acid esters, hydroxyl groups, amide-groups, amino groups, nitrile groups and quaternary ammonium salt groups. These non-acid monomers are well known materials and are described in greater detail, for example, in U.S. Pat. No. 4,076,663 issued to Masuda et al. on Feb. 28, 1978 and in U.S. Pat. No. 4,062,817 issued to Westerman on Dec. 13, 1977, both of which are incorporated herein by reference.

Olefinically unsaturated carboxylic acid and carboxylic acid anhydride monomers include the acrylic acids typified by acrylic acid itself, methacrylic acid, ethacrylic acid, alpha-chloroacrylic acid, alpha-cyano acrylic acid, beta-methyl acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-steryl acrylic acid, itaconic acid, citraconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyltoluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

Preferred polymer materials for use in the present invention possess a carboxyl group. These polymers include hydrolyzed starch-acrylonitrile graft copolymer, partially neutralized starch-acrylonitrile graft copolymer, starch-acrylic acid graft copolymer, partially neutralized starch-acrylic acid graft copolymer, saponified vinyl acetate-acrylic ester copolymers, hydrolyzed acrylonitrile or acrylamide copolymers, slightly network crosslinked products of any of the foregoing copolymers, partially neutralized polyacrylic acid, and slightly network crosslinked products of partially neutralized polyacrylic acid. These polymers may be used either independently or in the form of a mixture of two or more monomers, compounds, or the like. Examples of these polymer materials are disclosed in U.S. Pat. Nos. 3,661,875; 4,076,663; 4,093,776; 4,666,983; and 4,734,478.

Most preferred polymer materials for use as the precursor particles are slightly network crosslinked products of partially neutralized polyacrylic acids and starch derivatives therefrom. Most preferably, the precursor particles comprise from about 50 to about 95%, preferably about 75%, neutralized, slightly network crosslinked, polyacrylic acid (i.e., poly (sodium acrylate/acrylic acid)).

As described above, the precursor particles preferably are polymer materials that are slightly network crosslinked. Network crosslinking serves to render the precursor particles substantially water-insoluble and in part serves to determine the absorptive capacity and extractable polymer content characteristics of the precursor particles and the resultant macrostructure. Processes for network crosslinking the polymers and typical network crosslinking agents are described in greater detail in the hereinbefore-referenced U.S. Pat. No. 4,076,663.

The individual precursor particles may be formed in any conventional manner. Typical and preferred processes for producing the individual precursor particles are described in: U.S. Pat. No. Re. 32,649 entitled "Hydrogel-Forming Polymer Compositions For Use In Absorbent Structures" reissued to Kerryn A. Brandt, Steven A. Goldman, and Thomas A. Inglin on Apr. 19, 1988; U.S. Pat. No. 4,666,983 entitled "Absorbent Article" issued to Tsuneo Tsubakimoto, Tadao Shimomura, and Yoshio Irie on May 19, 1987; and U.S. Pat. No. 4,625,001 entitled "Method For Continuous Production Of Cross-Linked Polymer" issued to Tsuneo Tsubakimoto, Tadao Shimomura, and Yoshio Irie on Nov. 25, 1986. These patents are incorporated herein by reference.

Preferred methods for forming the precursor particles are those that involve aqueous solution or other solution polymerization methods. As described in the above-referenced U.S. Pat. No. Re. 32,649, aqueous solution polymerization involves the use of an aqueous reaction mixture to carry out polymerization to form the precursor particles. The aqueous reaction mixture is then subjected to polymerization conditions which are sufficient to produce in the mixture, substantially water-insoluble, slightly network crosslinked polymer material. The mass of polymer material thereby formed is then pulverized or chopped to form the individual precursor particles.

More specifically, the aqueous solution polymerization method for producing the individual precursor particles comprises the preparation of an aqueous reaction mixture in which to carry out polymerization to form the desired precursor particles. One element of such a reaction mixture is the acid group-containing monomer material which will form the "backbone" of the precursor particles to be produced. The reaction mixture will generally comprise about 100 parts by weight of the monomer material. Another component of the aqueous reaction mixture comprises a network crosslinking agent. Network crosslinking agents useful in forming the precursor particles are described in more detail in the above-referenced U.S. Pat. No. Re. 32,649 issued to Brandt et al.; U.S. Pat. No. 4,666,983 issued to Tsubakimoto et al.; and U.S. Pat. No. 4,625,001 issued to Tsubakimoto et al.. The network crosslinking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer material). An optional component of the aqueous reaction mixture comprises a free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomer materials including esters of the essential unsaturated acidic functional group-containing monomers or other co-monomers containing no carboxyl or sulfonic acid functionalities at all.

The aqueous reaction mixture is subjected to polymerization conditions which are sufficient to produce in the mixture substantially water-insoluble, absorbent, hydrogel-forming, slightly network crosslinked polymer materials. The polymerization conditions are also discussed in more detail in the three above-referenced patents. Such polymerization conditions generally involve heating (thermal activation techniques) to a polymerization temperature from about 0° C. to about 100° C., more preferably from about 5° C. to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques.

The acid functional groups of the polymer materials formed in the aqueous reaction mixture are also preferably neutralized. Neutralization can be carried out in any conventional manner which results in at least about 25 mole percent, and more preferably at least about 50 mole percent, of the total monomer utilized to form the polymer material being acid group-containing monomers that are neutralized with a salt-forming cation. Such salt-forming cations include, for example, alkali metals, ammonium, substituted ammonium and amines as discussed in further detail in the above-referenced U.S. Pat. No. Re. 32,649 issued to Brandt et al..

While it is preferred that the precursor particles be manufactured using an aqueous solution polymerization process, it is also possible to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. The resultant precursor particles are generally spherical in shape. Inverse suspension polymerization procedures are described in greater detail in U.S. Pat. No. 4,340,706 issued to Obaysashi et al. on Jul. 20, 1982; U.S. Pat. No. 4,506,052 issued to Flesher et al. on Mar. 19, 1985; and U.S. Pat. No. 4,735,987 issued to Morita et al. on Apr. 5, 1988; each of these patents being incorporated herein by reference.

In preferred embodiments of the present invention, the precursor particles used to form the interparticle crosslinked aggregate are substantially dry. The term "substantially dry" is used herein to mean that the precursor particles have a liquid content, typically water or other solution content, less than about 50%, preferably less than about 20%, more preferably less than about 10%, by weight of the precursor particles. In general, the liquid content of the precursor particles is in the range of from about 0.01% to about 5% by weight of the precursor particles. The individual precursor particles can be dried by any conventional method such as by heating. Alternatively, when the precursor particles are formed using an aqueous reaction mixture, water can be removed from the reaction mixture by azeotropic distillation. The polymer-containing aqueous reaction mixture can also be treated with a dewatering solvent such as methanol. Combinations of these drying procedures may also be used. The dewatered mass of polymer material can then be chopped or pulverized to form substantially dry precursor particles of substantially water-insoluble, absorbent, hydrogel-forming, polymer material.

Preferred precursor particles of the present invention are those which exhibit a high absorptive capacity so that the resultant macrostructure formed from such precursor particles also has a high absorptive capacity. Absorptive capacity refers to the capacity of a given polymer material to absorb liquids with which it comes into contact. Absorptive capacity can vary significantly with the nature of the liquid being absorbed and with the manner in which the liquid contacts the polymer material. For purposes of this invention, Absorptive Capacity is defined in terms of the amount of Synthetic Urine (as hereinafter defined) absorbed by any given polymer material in terms of grams of Synthetic Urine per gram of polymer material in a procedure hereinafter defined in the Test Methods section. Preferred precursor particles of the present invention are those which have an Absorptive Capacity of at least about 20 grams, more preferably at least about 25 grams, of Synthetic Urine per gram of polymer material. Typically, the polymer materials of the precursor particles herein have an Absorptive Capacity of from about 40 grams to about 70 grams of Synthetic Urine per gram of polymer material. Precursor particles having this relatively high absorptive capacity characteristic produce macrostructures that are especially useful in absorbent products, absorbent members, and absorbent articles since the resultant macrostructures formed from such precursor particles can, by definition, hold desirably high amounts of discharged body exudates such as urine.

The individual precursor particles may optionally be surface treated. For example, U.S. Pat. No. 4,824,901 issued to Alexander et al. on Apr. 25, 1989, discloses the surface treatment of polymeric particles with a polyquaternary amine. If surface treated, the precursor particles are preferably surface crosslinked as disclosed in U.S. Pat. No. 4,666,983, entitled "Absorbent Article", issued to Tsubakimoto et al. on May 19, 1987; and U.S. Pat. No. 4,734,478, entitled "Water Absorbing Agent" issued to Tsubakimoto et al. on Mar. 29, 1988; which patents are incorporated herein by reference. As disclosed in the Tsubakimoto et al. '983 patent, the individual precursor particles may be surface crosslinked by applying a surface crosslinking agent onto the precursor particles and reacting the surface crosslinking agent with the polymer material on the surface of the precursor particles.

While all of the precursor particles of the interparticle crosslinked aggregate are preferably formed of the same polymer material with the same properties, this need not be the case. For example, some precursor particles may comprise a polymer material of a starch-acrylic acid graft copolymer while other precursor particles may comprise a polymer material of slightly network crosslinked products of partially neutralized polyacrylic acid. Further, the precursor particles of the interparticle crosslinked aggregate may vary in shape, absorptive capacity, or any other property or characteristic of the precursor particles. In a preferred embodiment of the present invention, the precursor particles comprise a polymer material consisting essentially of slightly network crosslinked products of partially neutralized polyacrylic acid; each precursor particle having similar properties.

The interparticle crosslinked aggregate of the present invention also comprises an interparticle crosslinking agent. The interparticle crosslinking agent is applied onto the precursor particles and reacted with the polymer material of the precursor particles while physical association between the precursor particles is maintained. This reaction forms crosslink bonds between the precursor particles. Thus, the crosslink bonds are interparticle in nature (i.e., between different precursor particles). Without wishing to be bound by theory or limit the scope of the invention, it is believed the reaction of the interparticle crosslinking agent with the polymer material of the precursor particles forms crosslink bonds between the polymer chains of different precursor particles (i.e., interparticle crosslink bonds). For the preferred polymers herein, it is believed the interparticle crosslinking agent reacts to form crosslink bonds between the carboxyl groups of the previously independent precursor particles. Without wishing to be bound by theory or limit the scope of the invention, for the preferred polymer materials possessing carboxyl groups, it is believed that the interparticle crosslinking agent reacts with the carboxyl groups of the polymer materials to form covalent chemical crosslink bonds between the polymer chains of different precursor particles. The covalent chemical crosslink bonds generally arise as a result of the formation of ester, amide (imide) or urethane groups by reaction of the functional groups of the crosslinking agents with the carboxyl groups of the polymer material. In preferred executions, it is believed that ester bonds are formed. Thus, preferred interparticle crosslinking agents are those agents capable of reacting with the carboxyl groups in the preferred polymers to form ester bonds.

Interparticle crosslinking agents useful in the present invention are those that react with the polymer material of the precursor particles used to form the interparticle crosslinked aggregates. Suitable interparticle crosslinking agents may comprise a number of different agents such as, for example, compounds having at least two polymerizable double bonds; compounds having at least one polymerizable double bond and at least one functional group reactive with the polymer material; compounds having at least two functional groups reactive with the polymer material; or polyvalent metal compounds. Specific crosslinking agents useful in the present invention are described in more detail in the hereinbefore referenced U.S. Pat. No. 4,076,663 and U.S. Pat. No. Re. 32,649 which are incorporated herein by reference. The interparticle crosslinking agents may also comprise monomers (such as previously described) reactive with the polymer material of the precursor particles to form polymeric crosslink bonds.

Where carboxyl groups are present on or in the polymer material (i.e., the polymer chains) of the precursor particles, preferred interparticle crosslinking agents are solutions possessing at least two functional groups per molecule capable of reacting with the carboxyl group. Preferred interparticle crosslinking agents include polyhydric alcohols such as ethylene glycol, diethylene glycol, triethylene glycol, tetraethylene glycol, polyethylene glycol, glycerol (1,2,3-propanetriol), polyglycerol, propylene glycol (1,2propanediol), 1,3-propanediol, trimethylol propane, diethanolamine, triethanolamine, polyoxypropylene oxyethylene-oxypropyle block copolymer, sorbitan fatty acid esters, polyexyethylene sorbitan fatty acid esters, pentaerythritol, and sorbitol; polyglycidyl ether compounds such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether, and propylene glycol diglycidyl ether; polyaziridine compounds such as 2,2-bishydroxymethyl butanol-tris[3-(i-aziridine) propionate], 1,6-hexamethyl tolulene diethylene urea, and diphenyl methane-bis-4, 4'-N,N'-diethylene urea; haloepoxy compounds such as epichlorohydrin and α-methylfluorohydrin; polyaldehyde compounds such as glutaraldehyde and glyoxazole, polyamine compounds such as ethylene diamine, diethylene triamine, triethylene tetramine, tetraethylene pentamine, pentaethylene hexamine, and polyethylene imine; and polyisocyanate compounds such as 2,4-toluene diisocyanate and hexamethylene diisocyanate.

One interparticle crosslinking agent or two or more substantially mutually unreactive interparticle crosslinking agents selected from the group mentioned above may be used. Particularly preferred interparticle crosslinking agents for use herein with carboxyl-containing polymer material are ethylene glycol; glycerol; trimethylol propane; 1,2-propanediol; and 1,3-propanediol.

The proportion of the interparticle crosslinking agent to be used in the present invention is in the range of from about 0.01 parts to about 30 parts by weight, preferably from about 0.5 parts to about 10 parts by weight, most preferably from about 1 part to about 5 parts by weight, per 100 parts by weight of the precursor particles.

In the present invention, other materials or agents can be used with the interparticle crosslinking agent(s) as an aid in producing the interparticle crosslinked aggregate, or in promoting or assisting in the reaction of the interparticle crosslinking agent with the polymer material of the precursor particles, or as associating agents.

For example, water may be used in conjunction with the interparticle crosslinking agent. The water functions to promote uniform dispersion of the interparticle crosslinking agent on the surface of the precursor particles and permeation of the interparticle crosslinking agent into the surface region of the precursor particles. The water also promotes stronger physical association between the precursor particles of the prereacted aggregates, and the dry and swollen integrity of the resultant interparticle crosslinked aggregates. In the present invention, the water is used in a proportion of less than about 20 parts by weight (0 parts to about 20 parts by weight), preferably in the range of from about 0.01 parts to about 20 parts by weight, more preferably in the range of from about 0.1 parts to about 10 parts by weight, based on 100 parts by weight of the precursor particles. The actual amount of water to be used will vary depending upon the kind of polymer material and the particle size of the precursor particles.

Organic solvents may also be used in conjunction with the interparticle crosslinking agent. The organic solvents are used to promote uniform dispersion of the interparticle crosslinking agent on the surface of the precursor particles. The organic solvents are preferably hydrophilic organic solvents. The hydrophilic organic solvents useful in the present invention include lower alcohols such as methanol, ethanol, n-propanol, isopropanol, n-butanol, isobutanol, sec-butanol and t-butanol; ketones such as acetone, methylethyl ketone, and methylisobutyl ketone; ethers such as dioxane, tetrahydrofuran, and diethyl ether; amides such as N, N-dimethylformamide and N, N-diethylformamide; and sulfoxides such as dimethyl sulfoxide. The hydrophilic organic solvent is used in the present invention in a proportion of less than about 60 parts by weight (0 parts to about 60 parts by weight), preferably in the range of from about 0.01 parts to about 60 parts by weight, more preferably from about 1 part to about 20 parts by weight, based on 100 parts by weight of the precursor particles. The actual amount of hydrophilic organic solvent to be used will vary depending upon the kind of polymer material and the particle size of the precursor particles.

The interparticle crosslinking agent may also be used in a mixture with water and one or more hydrophilic organic solvents. It has been found that the use of a water/interparticle crosslinking agent solution provides the greatest penetration of the crosslinker into the surface region of the precursor particles while a solution of hydrophilic organic solvent/interparticle crosslinking agent provides minimal penetration of the crosslinker. However, a mixture of all three agents is preferred in order to control the amount of the penetration of the interparticle crosslinking agent into the surface region of the precursor particles. Specifically, it has been found that the higher the water to organic solvent component ratio, the deeper the crosslinker penetration, the greater the fluid stability of the macrostructure under stress, and the greater the reduction in the resultant absorptive capacity of the macrostructure. Typically, the ratio of water to hydrophilic organic solvent in the solution will be in the range of from about 10:1 to about 1:10. The hydrophilic organic solvent/water/interparticle crosslinking agent solution is used in a proportion less than about 60 parts by weight (0 parts to about 60 parts by weight), preferably in the range of from about 0.01 parts to about 60 parts by weight, more preferably from about 1 part to about 20 parts by weight, based on 100 parts by weight of the precursor particles.

Other optional components may also be mixed with the solution containing the interparticle crosslinking agent. For example, an initiator, a catalyst, or non-acid co-monomer materials may be added. Examples of these materials suitable for use herein are described in the hereinbefore referenced U.S. Pat. No. Re. 32,649.

The method of producing the porous, absorbent, polymeric macrostructure comprising an interparticle crosslinked aggregate comprises the steps of providing precursor particles of the type herein described; applying an interparticle crosslinking agent to a portion of the precursor particles; physically associating the precursor particles to form an aggregate; shaping the aggregate; and reacting the interparticle crosslinking agent with the polymer material of the precursor particles of the aggregate, while maintaining the physical association of the precursor particles, to form crosslink bonds between the polymer chains of different precursor particles.

The interparticle crosslinking agent is applied onto the precursor particles. The interparticle crosslinking agent may be applied by any of various techniques and apparatus used for applying solutions to materials including coating, dumping, pouring, dropping, spraying, atomizing, condensing, or immersing the interparticle crosslinking agent onto the precursor particles. As used herein, the term "applied onto" means that at least a portion of the surface area of at least one of the precursor particles to be joined has the interparticle crosslinking agent on it. Thus, the interparticle crosslinking agent may be applied onto only some of the precursor particles, onto all of the precursor particles, onto only a portion of the surface of some or all of the precursor particles, or onto the entire surface of some or all of the precursor particles. Preferably, the interparticle crosslinking agent is coated onto the entire surface of most, preferably all, of the precursor particles so as to enhance the efficiency, strength, and density of the interparticle crosslink bonds between the precursor particles.

In the preferred embodiments of the present invention, after the interparticle crosslinking agent has been applied onto the precursor particles, the interparticle crosslinking agent is mixed with the precursor particles by any of a number of mixing techniques to insure that the precursor particles are thoroughly coated with the interparticle crosslinking agent. Because the precursor particles are thoroughly coated with the interparticle crosslinking agent, the efficiency, strength, and density of the crosslink bonds between the precursor particles are enhanced. The mixing can be accomplished using various techniques and apparatus, including various mixers or kneaders, as are known in the art.

Before, during, or after applying the interparticle crosslinking agent onto the precursor particles, the precursor particles are physically associated together to form an aggregate macrostructure. The term "physically associated" is used herein to mean that the precursor particles are brought together and remain in contact with each other as component parts in any of a number of various ways and spatial relationships so as to form a single unit (an aggregate macrostructure).

The precursor particles are preferably physically associated together by applying an associating agent onto the precursor particles and physically contacting the precursor particles at at least the portion of the surface of the precursor particles having the associating agent applied thereto. Preferred associating agents cause the polymer material of the precursor particles, when brought together, to adhere together by the action of fluid surface tension forces and/or the entanglement of polymer chains due to external swelling. Associating agents useful in the present invention include hydrophilic organic solvents, typically low molecular weight alcohols such as methanol, ethanol, or isopropanol; water; a mixture of hydrophilic organic solvents and water; certain interparticle crosslinking agents as hereinbefore described; volatile hydrophobic organic compounds such as hexane, octane, benzene or toluene; or mixtures thereof. Preferred associating agents are water, methanol, isopropanol, ethanol, interparticle crosslinking agents such as glycerol, or mixtures thereof. Typically the associating agent comprises a mixture including an interparticle crosslinking agent such that the step of applying an interparticle crosslinking agent is carried out simultaneously with the step of applying an associating agent.

The associating agents may be applied to the precursor particles by any of various techniques and apparatus used for applying solutions to materials including coating, dumping, pouring, spraying, atomizing, condensing, or immersing the associating agent on the precursor particles. The associating agent is applied onto at least a portion of the surface area of at least one of the precursor particles to be joined per aggregate. Preferably, the associating agent is coated onto the entire surface of most, preferably all, of the precursor particles. The associating agent is generally mixed with the precursor particles by any of a number of mixing techniques and mixing apparatus to insure that the precursor particles are thoroughly coated with the associating agent.

When an associating agent has been applied to the precursor particles, the precursor particles may be physically contacted together in a number of different ways. For example, the associating agent alone may hold the particles together in contact. Alternatively, gravitational forces may be used to insure contact between the precursor particles. Further, the particles may be placed in a container having a fixed volume so as to insure contact between the precursor particles.

The precursor particles can alternatively be physically associated together by physically constraining the precursor particles such that they are in contact with each other. For example, the precursor particles may be packed tightly into a container having a fixed volume such that the precursor particles physically contact each other. Alternatively or in combination with the above procedure, gravitational forces may be used to physically associate the precursor particles. The precursor particles may also be physically associated together via electrostatic attraction or by the introduction of an adhering agent (e.g., an adhesive material such as a water-soluble adhesive) to adhere them together. The precursor particles may also be attached to a third member (a substrate) such that the precursor particles are brought into contact with each other by the substrate.

In an alternative and preferred step in forming the macrostructures of the present invention, the aggregate of the precursor particles is shaped into various geometries, spatial relationships, and densities to form an aggregate having a defined shape, size, and/or density. The aggregate may be shaped by any conventional shaping techniques as are known in the art. Preferred methods for shaping the aggregate include casting, molding, or forming operations. Casting and molding techniques generally involve introducing the precursor particles into a prepared mold cavity and applying pressure to (compressing) the aggregate to cause the aggregate to conform to the shape of the mold cavity. Examples of specific molding techniques for use herein include compression molding, injection molding, extrusion or laminating. For example, a multiplicity of precursor particles may be added to a container having a fixed volume mold cavity and the aggregate compressed to conform to the shape of the mold cavity so that the resultant macrostructure has a shape defined by the shape of the mold cavity. Forming techniques involve performing various operations on the aggregate to modify its shape, and/or size, and/or density. Examples of specific forming techniques for use herein include rolling, forging, extruding, spinning, coating or drawing operations. For example, an aggregate mixture of the precursor particles and at least the interparticle crosslinking agent may by passed between a pair of compaction rolls to form a sheet aggregate. Alternatively, the aggregate mixture may by extruded through an orifice to form an aggregate having a shape corresponding to the shape of the orifice. Further, the aggregate mixture may be cast on a surface to form an aggregate having a desired shape or surface morphology. Any or all of these techniques may also be used in combination to form the shaped aggregate. Any suitable apparatus as are known in the art may be used to carry out such operations, and the operation may be performed with the material or portions of the apparatus either hot and/or cold.

In a preferred embodiment of the present invention, an aggregate mixture of precursor particles, an interparticle crosslinking agent, water, and a hydrophilic organic solvent are added to the hopper of a conventional extruder apparatus. An example of an extruder apparatus is shown in FIG. 12-14 of *Principles of Polymer Materials, Second Edition* (McGraw-Hill Book Company, 1982) at page 331, which publication is incorporated herein by reference. The aggregate mixture is extruded through the orifice of the extruder apparatus to feed a pair of driven compaction rolls having a fixed (but variable) gap between the rolls so as to compress the aggregate into the form of a sheet. The sheet is then processed to specific lengths to provide macrostructures that have a specifically designed size, shape, and/or density.

Simultaneously or after the interparticle crosslinking agent has been applied, the precursor particles have been physically associated together to form an aggregate, and the aggregate has been shaped, the interparticle crosslinking agent is reacted with the polymer material of the precursor particles of the aggregate, while maintaining the physical association of the precursor particles, to form crosslink bonds between the precursor particles to form an interparticle crosslinked aggregate macrostructure.

The reaction between the interparticle crosslinking agent and the polymer material must be activated and completed to form the crosslink bonds between different precursor particles to form the interparticle crosslinked aggregate. Although the crosslinking reaction may be activated by irradiation (e.g., ultraviolet, gamma- or X-radiation) or by a catalyst as an initiator and an activator, the crosslinking reaction is preferably thermally activated (heating). Heating activates and drives the reaction and drives off any volatiles present in the mixture. Such reaction conditions will generally involve heating the associated precursor particles and the interparticle crosslinking agent for certain times and at certain temperatures. The heating step can be carried out using a number of different apparatus as are known including the various ovens or driers as are known in the art.

Generally, the reaction is effected by heating to a temperature above about 90° C. for a sufficient time to complete the crosslinking reaction. For each set of specific interparticle crosslinking agent(s) and polymer material of the precursor particles used, if the temperature is too low or the time is too short, the reaction will not be sufficiently driven resulting in fewer and weaker interparticle crosslink bonds thereby causing some loss of liquid permeability of the macrostructure upon swelling. If the temperature is too high, the absorbency of the precursor particles may be degraded or the network crosslinks of these precursor particles, depending upon the specific polymer materials, may be degraded to such a point that the resultant macrostructure is not useful for absorbing large quantities of liquids. In addition, if the time and temperatures are not correct, the extractable levels of the resultant aggregates may increase, thereby increasing the incidence of that form of gel blocking. Therefore, the reaction will generally be carried out at a temperature in the range from about 120° C. to about 300° C., more preferably from about 100° C. to about 250° C. The time to complete the reaction, in the absence of catalysts, will generally be from about 5 minutes to about 6 hours, more preferably from about 10 minutes to about 4 hours.

For the preferred polymer material of the precursor particles, slightly network crosslinked products of partially neutralized polyacrylic acid, and the preferred interparticle crosslinking agents, such as glycerol or trimethylol propane, such reaction conditions will involve a temperature of from about 170° C. to about 220° C. for about 3 hours to about 30 minutes, respectively. More preferably, the reaction is carried out at a temperature between about 190° C. to about 210° C. for about 75 minutes to about 45 minutes, respectively. The actual time and temperatures used will vary depending upon the specific polymer materials used for the precursor particles, the specific interparticle crosslinking agents used, the presence or absence of a catalyst used to drive the reaction, and the thickness or diameter of the macrostructure.

The crosslinking reaction can be promoted by adding an initiator and/or a catalyst to the interparticle crosslinking agent to reduce the time and/or the temperature and/or the amount of interparticle crosslinking agent required to join the precursor particles together. Generally, however, the reaction is conducted in the absence of a catalyst.

The physical association of the precursor particles needs to be maintained during the reaction step so that sufficient interparticle crosslink bonds are formed. If forces or stresses sufficient to dissociate the precursor particles are present during the reaction step, the crosslink bonds between the precursor particles (interparticle crosslink bonds) may not be formed. The physical association of the precursor particles is typically maintained by insuring minimal dissociation forces or stresses are introduced during the reaction step.

As an optional and preferred step in the method of forming the porous, absorbent, polymeric macrostructure, the component precursor particles of the macrostructure are surface treated. For example, U.S. Pat. No. 4,824,901 issued to Alexander et al. on Apr. 25, 1989, discloses the surface treatment of polymeric particles with a poly-quaternary amine. In an exemplary method, the polymer material existing at least in the vicinity of the surface of the precursor particles is surface crosslinked such as disclosed in U.S. Pat. No. 4,666,983, entitled "Absorbent Article" issued to Tsubakimoto et al. on May 19, 1987; and U.S. Pat. No. 4,734,478, entitled "Water Absorbing Agent" issued to Tsubakimoto et al. on Mar. 29, 1988; which patents are incorporated herein by reference. By utilizing a surface crosslinking step in the present invention, the resistance to deformation of the resultant macrostructure, when swollen, is improved. Preferably, the interparticle crosslinking agent applied to the precursor particles also serves as the surface crosslinking agent such that the macrostructure is preferably simultaneously formed and surface crosslinked.

As previously discussed, the steps in the method for producing the macrostructure need not be carried out in any specific order. In addition, the steps may be carried out simultaneously.

In a preferred embodiment, the interparticle crosslinking agent is applied simultaneously with the physical association of the precursor particles, the mixture is subsequently shaped into a preferred shape and typically a desired density, and the interparticle crosslinking agent is subsequently reacted with the polymer material of the precursor particles, either immediately after the above steps are completed or after the aggregate has been left standing for a period of time, to simultaneously form and surface crosslink the macrostructure. Typically, the precursor particles are introduced into a vessel and mixed with a solution of an interparticle crosslinking agent, water, and a hydrophilic organic solvent atomized onto the precursor particles to form an aggregate. The interparticle crosslinking agent, water, and the hydrophilic organic solvent serves as an associating agent for the precursor particles. The interparticle crosslinking agent also serves as a surface crosslinking agent. The aggregate (i.e., the associated precursor particles and the aqueous mixture) are subsequently shaped into a densified sheet-form by a combination of extruding and rolling techniques as described above. The interparticle crosslinking agent is subsequently reacted by heating with the polymer material to form crosslink bonds between the precursor particles to form an interparticle crosslinked aggregate macrostructure and simultaneously to surface crosslink the surfaces of the precursor particles of the resultant macrostructure.

Under certain conditions, the resultant macrostructures can be somewhat inflexible and brittle. More flexible macrostructures can be obtained in several ways. For example, a plasticizer can be added to the macrostructure after the interparticle crosslinking reaction is complete. Suitable plasticizers include water, high molecular weight hydrophilic organic solvents (e.g., glycerol; 1,3-propanediol; or ethylene glycol), or polymeric solutions (e.g., polyvinyl alcohol or polyethylene glycol), or mixtures thereof. The plasticizer can be applied to the macrostructures in a number of different ways including spraying, coating, atomizing, immersing, or dumping the solution onto the macrostructure. Alternatively, in the case of water, the plasticizer may be added via placing the macrostructure into a high humidity environment (e.g., greater than 70% relative humidity). A plasticizer may also be added to the pre-reaction mixture containing a polymerizable monomer with the monomer being subsequently reacted to form interparticle polymeric crosslink bonds. In this case, the plasticizer is entrapped in the interparticle crosslink bond structures during the crosslinking reaction. The amount of plasticizer present in the solution is selected depending upon the specific plasticizer being used. Typically, the plasticizer comprises from about 0.01 parts to about 100 parts by weight of the plasticizer per 100 parts by weight of the precursor particles.

As shown in FIGS. 1-3, the resultant macrostructure has pores (the dark areas of the photomicrograph) between adjacent precursor particles. The pores are small interstices between adjacent precursor particles that allow the passage of liquid into the interior of the macrostructure. The pores are formed into the macrostructure because the precursor particles do not "fit" or pack tightly enough, even when compressed, to eliminate the pores. (The packing efficiency of the precursor particles is less than 1.) The pores are generally smaller than the constituent precursor particles and provide capillaries between the precursor particles to transport liquid into the interior of the macrostructure.

The pores are interconnected with each other by intercommunicating channels between the pores. The channels allow liquids contacting the macrostructure to be transported via capillary forces (i.e., capillary channels are formed) to other portions of the macrostructure so that the total volume of the macrostructure is used in absorbing such liquids. Further, when swollen, the pores and the intercommunicating channels allow liquids to pass through the macrostructure either to layers of precursor particles remote from the initial point of liquid contact or to other structures in contact with the macrostructure. Thus, the macrostructure is considered to be liquid permeable due to the pores and the intercommunicating channels.

The void fraction (i.e., the total volume of the macrostructure that comprises the pores and the channels) has a minimum value for a given precursor particle size distribution. In general, the narrower the precursor particle size distribution, the higher the void fraction will be. Thus, it is preferred, so as to provide higher void fractions in a densified state, that the precursor particles have a relatively narrow particle size distribution.

Another feature of the macrostructures of the present invention is that the macrostructures swell generally isotropically, even under moderate confining pressures, when liquids are deposited onto or come into contact with the macrostructures. Isotropic swelling is used herein to mean that the macrostructure swells generally equally in all directions when wetted. Isotropic swelling is an important property of the macrostructure because the precursor particles and the pores are able to maintain their relative geometry and spatial relationships even when swollen such that the existing capillary channels are maintained, if not enlarged, during use. (The pores and the precursor particles get larger during swelling.) Thus, the macrostructure can imbibe and/or transport through itself additional loadings of liquid while not gel blocking.

An indication that crosslink bonds are being formed in the macrostructure between the previously independent precursor particles is that the resultant macrostructures are fluid (i.e., liquid) stable. "Fluid stable" is used herein to mean a macrostructure comprising an interparticle crosslinked aggregate that upon contact with or swelling (with and/or without stress) in an aqueous fluid remains substantially intact (i.e., most of the previously independent component precursor particles remain joined together). While the definition of fluid stability recognizes that most of the precursor particles remain joined together, preferably all of the precursor particles used to make up the macrostructure remain joined together. However, it should be recognized that some of the precursor particles may dissociate themselves from the macrostructure if, for example, other particles have been subsequently water agglomerated to the macrostructure.

Fluid stability is an important feature of the macrostructures of the present invention because it allows the aggregate to maintain its relative structure in both the dry and swollen states, and because it immobilizes component precursor particles. In an end product such as an absorbent member or an absorbent article, fluid stability is beneficial in reducing gel blocking since precursor particles remain aggregated even when contacted with liquid, and allows one to use previously independent fine particles in an aggregate form to increase the rate of fluid uptake of the resultant macrostructure without introducing the element of gel blocking.

Fluid stability can be measured in an aggregate macrostructure by a two step process. The initial dynamic response of the aggregate macrostructure upon contact with the aqueous fluid is observed and then the fully swollen equilibrium condition of the aggregate macrostructure is observed. A test method for determining fluid stability based on these criteria is hereinafter described in the Test Methods section.

In use, liquids that are deposited onto or come in contact with the macrostructures are imbibed by the precursor particles or are passed into the pores and transmitted to other portions of the macrostructure where they are imbibed by other precursor particles or transported through the macrostructure to other absorbent members adjacent thereto.

Figure 4:
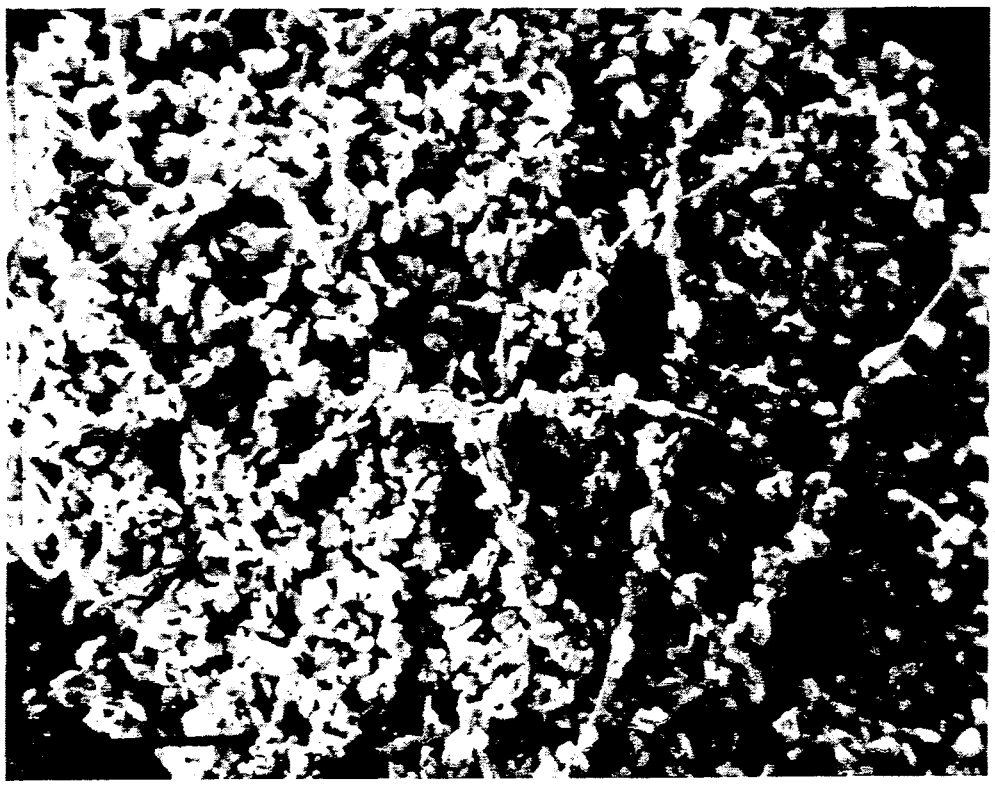
FIG. 4 is a photomicrograph enlarged approximately 20 times of a top view of a portion of an alternative embodiment of a porous, absorbent, polymeric macrostructure having superabsorbent fibers used in the macrostructure.
Figure 5:
FIG. 5 is a photomicrograph enlarged approximately 50 times of a top view of a portion of the macrostructure of FIG. 4.
Figure 6:
FIG. 6 is a photomicrograph enlarged approximately 75 times of a top view of a portion of the macrostructure of FIG. 4.

FIGS. 4-6 show an alternative embodiment of the present invention wherein the precursor particles comprise different shapes and chemistries. The precursor particles consist of a mixture of irregular-shaped granules and fibers (i.e., superabsorbent fibers). In the embodiment shown in FIGS. 4-6, the fibers are FIBERSORB fibers as available from the Arco Chemical Company of Wilmington, Del. FIG. 4 shows the general shape of such a macrostructure. As shown in FIG. 4, the fibers provide a matrix wherein relatively small pores are formed between the granules and relatively large pores are formed about the fibers. FIG. 5 shows more detail relating to the shape and size of the pores and that the granules are interparticle crosslinked to the fibers. FIG. 6 shows in more detail the large pores and channels formed in the macrostructure by the addition of the fibers and the particle/fiber bonding.

The relative amount of superabsorbent fibers mixed with the granules can vary widely. For example, the macrostructure may be formed of only the superabsorbent fibers; the resultant macrostructure having the appearance of nonwoven fiber webs. In the embodiments shown in FIGS. 4-6, the superabsorbent fibers comprise from about 0.1% to about 50%, more preferably from about 0.5% to about 10%, by weight of the total amount of precursor particles.

When superabsorbent fibers comprise a portion of the precursor particles, the fibers are preferably thoroughly mixed with the other precursor particles so that the fibers are interwoven between many different precursor particles.

Figure 7:
FIG. 7 is a photomicrograph enlarged approximately 100 times of a perspective view (45° from the horizontal) of a portion of an alternative embodiment of a porous, absorbent, polymeric macrostructure having polyester fibers embedded in the macrostructure.

FIG. 7 shows an alternative embodiment of a macrostructure of the present invention wherein reinforcing members such as fibers (fibrous or fiber material) are embedded in the macrostructure. The reinforcing members provide strength (i.e., structural integrity) to the swollen macrostructure. In certain embodiments, the reinforcing fibers also provide members that quickly wick liquids to other portions of the macrostructure and/or additional absorbent material. The reinforcing members preferably comprise fibers (also referred to as reinforcing fibers); although other materials such as filaments, coils, webs, nonwoven webs, woven webs, or scrims as are known for their reinforcing properites may be used. FIG. 7 shows an embodiment wherein polyester fibers are interwoven throughout the macrostructure. Specifically, the polyester fibers are contained within the intercommunicating channels to provide increased swollen structural integrity for the macrostructure.

Various types of fiber material can be used for the reinforcing members in the macrostructures of the present invention. Any type of fiber material which is suitable for use in conventional absorbent products is also suitable for use in the macrostructures herein. Specific examples of such fiber material include cellulose fibers, modified cellulose fibers, rayon, polypropylene, and polyester fibers such as polyethylene terephthalate (DACRON), hydrophilic nylon (HYDROFIL), and the like. Examples of other fiber materials for use in the present invention in addition to some already discussed are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the macrostructures of the present invention by virtue of their good wicking properties. This is because, in the macrostructures herein, the wicking propensity of the fibers is as important, if not more important, than the absorbent capacity of the fiber material itself due to the high rate of fluid uptake and lack of gel blocking properties of the macrostructures of the present invention. Synthetic fibers are generally preferred for use herein as the fiber component of the macrostructure. Most preferred are polyolefin fibers, preferably polyester fibers.

Other cellulosic fiber materials which may be useful in certain macrostructures herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Types of stiffened, twisted, curled cellulose fibers useful as the hydrophilic fiber material herein are described in greater detail in U.S. Pat. No. 4,888,093 entitled "Individualized, Crosslinked Fibers And Process For Making Said Fibers" issued to Dean et al. on Dec. 19, 1989; U.S. Pat. No. 4,889,595 entitled "Process For Making Individualized, Crosslinked Fibers Having Reduced Residuals And Fibers Thereof" issued to Herron et al. on Dec. 26, 1989; U.S. Pat. No. 4,889,596 entitled "Process For Making Individualized Crosslinked Fibers And Fibers Thereof" issued to Schoggen et al. on Dec. 26, 1989; U.S. Pat. No. 4,889,597 entitled "Process for Making Wet-Laid Structures Containing Individualized Stiffened Fibers" issued to Bourbon et al on Dec. 26, 1989; and U.S. Pat. No. 4,898,647 entitled "Twisted, Chemically Stiffened Fibers And Absorbent Structures Made Therefrom" issued to Moore et al. on Feb. 6, 1990. Each of these patents are incorporated herein by reference.

As used herein, the term "hydrophilic" describes fibers or the surfaces of fibers which are wetted by the liquids deposited onto the fibers (i.e., if water or aqueous body fluid readily spreads on or over the surface of the fiber without regard to whether or not the fiber actually imbibes fluid or forms a gel). The state of the art respecting wetting of materials allows definition of hydrophobicity (and wetting) in terms of contact angles and the surface tension of the liquids and solids involved. This is discussed in detail in the American Chemical Society Publication entitled *Contact Angle, Wettability, and Adhesion* edited by Robert F. Gould and copyrighted in 1964. A fiber or surface of a fiber is said to be wetted by a liquid either when the contact angle between the liquid and the fiber or surface is less than 90° or when the liquid will tend to spread spontaneously across the surface of the fiber; both conditions normally coexisting.

The fiber material may be added to the macrostructures by introducing the fibers into solution with the interparticle crosslinking agent, by mixing with the precursor particles prior to applying the interparticle crosslinking agent, or by adding the fiber material to the interparticle crosslinking agent/precursor particle mixture. In a preferred embodiment, the fiber material is kneaded into the interparticle crosslinking agent/precursor particle mixture. The fiber material is preferably thoroughly mixed with the solutions so that the fiber material is uniformly dispersed throughout the macrostructure. The fibers are also preferably added before reacting the interparticle crosslinking agent with the polymer material of the precursor particles.

The relative amount of fiber material mixed with the precursor particles can vary widely. The fiber material is preferably added in a range from about 0.01 parts to about 5 parts, more preferably in the range of from about 0.5 parts to about 2 parts, by weight per 100 parts by weight of the precursor particles.

The porous, absorbent, polymeric macrostructures can be used for many purposes in many fields of use. For example, the macrostructures can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, dessicants, and humidity control materials.

The porous, absorbent, polymeric macrostructures of the present invention are useful when joined to a carrier. Carriers useful in the present invention include absorbent materials such as cellulose fibers. The carriers also may be any other carriers as are known in the art such as nonwoven webs, tissue webs, foams, polyacrylate fibers, apertured polymeric webs, synthetic fibers, metallic foils, elastomers, and the like. The macrostructures may be joined directly or indirectly to the carriers and may be joined thereto via chemical or physical bonding such as are known including adhesives or chemicals that react to adhere the macrostructures to the carriers.

Figure 8:
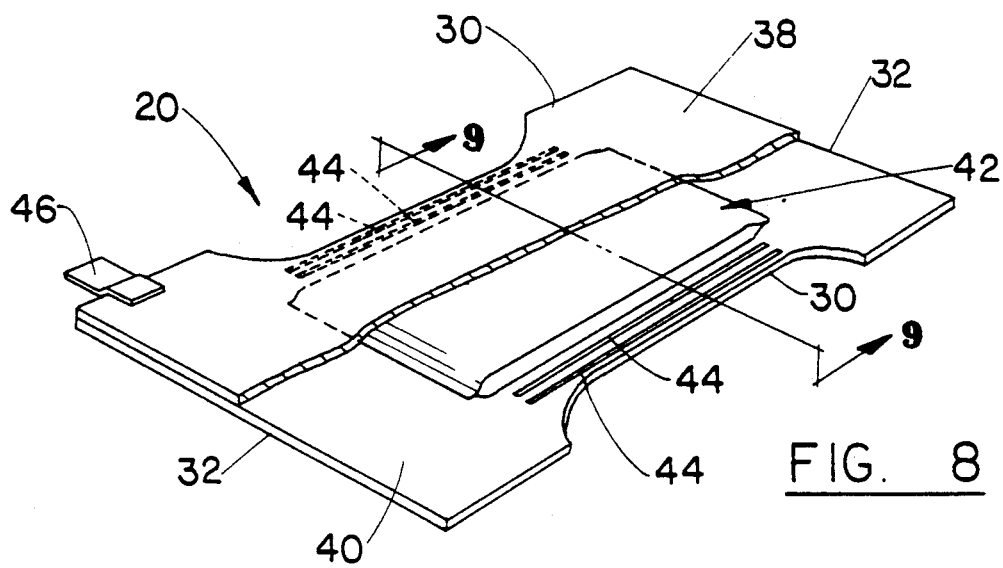
FIG. 8 is a perspective view of a disposable diaper embodiment of the present invention wherein portions of the topsheet have been cut-away to more clearly show the underlying absorbent core (an embodiment of an absorbent member of the present invention) of the diaper wherein the absorbent member comprises a porous, absorbent, polymeric macrostructure of the present invention.

Because of the unique absorbent properties of the porous, absorbent, polymeric macrostructures of the present invention, the macrostructures are especially suitable for use as absorbent cores in absorbent articles, especially disposable absorbent articles. As used herein, the term "absorbent article" refers to articles which absorb and contain body exudates and more specifically refers to articles which are placed against or in proximity to the body of the wearer to absorb and contain the various exudates discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). A preferred embodiment of a disposable absorbent article, diaper 20, is shown in FIG. 8. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like.

FIG. 8 is a perspective view of the diaper 20 of the present invention in its uncontracted state (i.e., with all the elastic induced contraction removed) with portions of the structure being cut-away to more clearly show the construction of the diaper 20 and with the portion of the diaper 20 which contacts the wearer facing the viewer. The diaper 20 is shown in FIG. 8 to preferably comprise a liquid pervious topsheet 38; a liquid impervious backsheet 40 joined with the topsheet 38; an absorbent core 42 positioned between the topsheet 38 and the backsheet 40; elastic members 44; and tape tab fasteners 46. While the topsheet 38, the backsheet 40, the absorbent core 42, and the elastic members 44 may be assembled in a variety of well known configurations, a preferred diaper configuration is described generally in U.S. Pat. No. 3,860,003 entitled "Contractable Side Portions For Disposable Diaper", which issued to Kenneth B. Buell on Jan. 14, 1975, and which patent is incorporated herein by reference. Alternatively preferred configurations for disposable diapers herein are also disclosed in U.S. Pat. No. 4,808,178 entitled "Disposable Absorbent Article Having Elasticized Flaps Provided With Leakage Resistant Portions" issued to Mohammed I. Aziz and Ted L. Blaney on Feb. 28, 1989; U.S. Pat. No. 4,695,278 entitled "Absorbent Article Having Dual Cuffs" issued to Michael I. Lawson on Sept. 22, 1987; and U.S. Pat. No. 4,816,025 entitled "Absorbent Article Having A Containment Pocket" issued to John H. Foreman on Mar. 28, 1989. These patents are incorporated herein by reference.

FIG. 8 shows a preferred embodiment of the diaper 20 in which the topsheet 38 and the backsheet 40 are co-extensive and have length and width dimensions generally larger than those of the absorbent core 42. The topsheet 38 is joined with and superimposed on the backsheet 40 thereby forming the periphery of the diaper 20. The periphery defines the outer perimeter or the edges of the diaper 20. The periphery comprises the end edges 32 and the longitudinal edges 30.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent core 42.

A particularly preferred topsheet 38 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which may be used to manufacture the topsheet 38. For example, the topsheet 38 may be woven, nonwoven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction, and a wet tensile strength of at least about 55 grams per centimeter in the cross-machine direction.

The backsheet 40 is impervious to liquids and is preferably manufactured from a thin plastic film, although other flexible liquid impervious materials may also be used. The backsheet 40 prevents the exudates absorbed and contained in the absorbent core 42 from wetting articles which contact the diaper 20 such as bedsheets and undergarments. Preferably, the backsheet 40 is polyethylene film having a thickness from about 0.012 mm (0.5 mil) to about 0.051 centimeters (2.0 mils), although other flexible, liquid impervious materials may be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent core 42 while still preventing exudates from passing through the backsheet 40.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 centimeters to about 2.5 centimeters (about 0.5 to about 1.0 inch) around the entire diaper periphery.

The topsheet 38 and the backsheet 40 are joined together in any suitable manner. As used herein, the term "joined" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate members which in turn are affixed to the backsheet 40. In a preferred embodiment, the topsheet 38 and the backsheet 40 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive may be used to affix the topsheet 38 to the backsheet 40.

Tape tab fasteners 46 are typically applied to the back waistband region of the diaper 20 to provide a fastening means for holding the diaper on the wearer. The tape tab fasteners 46 can be any of those well known in the art, such as the fastening tape disclosed in U.S. Pat. No. 3,848,594 issued to Kenneth B. Buell on Nov. 19, 1974, which patent is incorporated herein by reference. These tape tab fasteners 46 or other diaper fastening means are typically applied near the corners of the diaper 20.

The elastic members 44 are disposed adjacent the periphery of the diaper 20, preferably along each longitudinal edge 30, so that the elastic members 44 tend to draw and hold the diaper 20 against the legs of the wearer. Alternatively, the elastic members 44 may be disposed adjacent either or both of the end edges 32 of the diaper 20 to provide a waistband as well as or rather than leg cuffs. For example, a suitable waistband is disclosed in U.S. Pat. No. 4,515,595 entitled "Disposable Diapers with Elastically Contractible Waistbands" which issued to David J. Kievit and Thomas F. Osterhage on May 7, 1985, which patent is herein incorporated by reference. In addition, a method and apparatus suitable for manufacturing a disposable diaper having elastically contractible elastic members is described in U.S. Pat. No. 4,081,301 entitled "Method and Apparatus for Continuously Attaching Discrete, Stretched Elastic Strands to Predetermined Isolated Portions of Disposable Absorbent Products" which issued to Kenneth B. Buell on Mar. 28, 1978 and which patent is incorporated herein by reference.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For example, the elastic members 44 may be stretched and secured while the diaper 20 is in an uncontracted condition. Alternatively, the diaper 20 may be contracted, for example, by pleating, and the elastic members 44 secured and connected to the diaper 20 while the elastic members 44 are in their unrelaxed or unstretched condition.

In the embodiment illustrated in FIG. 8, the elastic members 44 extend along a portion of the length of the diaper 20. Alternatively, the elastic members 44 may extend the entire length of the diaper 20, or any other length suitable to provide an elastically contractible line. The length of the elastic member$ 44 is dictated by the diaper design.

The elastic members 44 may take a multitude of configurations. For example, the width of the elastic members 44 may be varied from about 0.25 millimeters (0.01 inches) to about 25 millimeters (1.0 inch) or more; the elastic members 44 may comprise a single strand of elastic material or may comprise several parallel or non-parallel strands of elastic material; or the elastic members 44 may be rectangular or curvilinear. Still further, the elastic members 44 may be affixed to the diaper in any of several ways which are known in the art. For example, the elastic members 44 may be ultrasonically bonded, heat and pressure sealed into the diaper 20 using a variety of bonding patterns or the elastic members 44 may simply be glued to the diaper 20.

The absorbent core 42 of the diaper 20 is positioned between the topsheet 38 and the backsheet 40. The absorbent core 42 may be manufactured in a wide variety of sizes and shapes (e.g., rectangular, hourglass, asymmetrical, etc.) and from a wide variety of materials. The total absorbent capacity of the absorbent core 42 should, however, be compatible with the design liquid loading for the intended use of the absorbent article or diaper. Further, the size and absorbent capacity of the absorbent core 42 may vary to accommodate wearers ranging from infants through adults. The absorbent core 42 comprises the porous, absorbent, polymeric macrostructures of the present invention.

Figure 9:
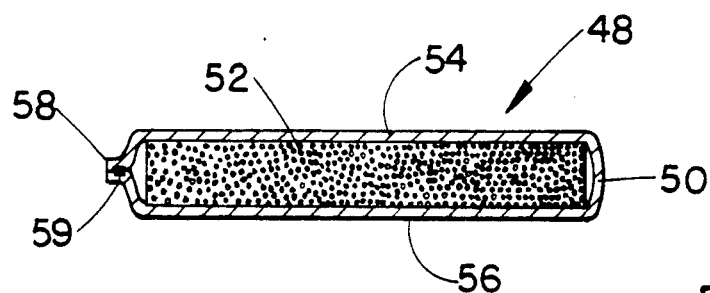
FIG. 9 is a cross-sectional view of the absorbent core of the diaper shown in FIG. 8 taken along sectional line 9—9 of FIG. 8.

A preferred embodiment of the diaper 20 has a rectangular-shaped absorbent core 42. As shown in FIG. 9, the absorbent core 42 preferably comprises an absorbent member 48 comprising an envelope web 50 and a porous, absorbent, polymeric macrostructure 52 disposed in the envelope web 50. The macrostructure 52 is encased in the envelope web 50 to minimize the potential for the precursor particles to migrate through the topsheet and to provide an additional liquid transport layer between the topsheet 38 and the macrostructure 52 to enhance liquid acquisition and minimize rewet. As shown in FIG. 9, a single envelope web 50 is wrapped about the macrostructure 52 by folding to form a first layer 54 and a second layer 56. The edges 58 of the envelope web 50 are sealed about its periphery by any conventional means such as an adhesive 59 (as shown), ultrasonic bonds, or heat/pressure bonds, to form a pouch. The envelope web 50 may comprise a number of materials including nonwoven webs, paper webs, or webs of absorbent materials such as tissue paper. The envelope web 50 preferably comprises a nonwoven web similar to the webs used to form the topsheet 38. The nonwoven web is preferably hydrophilic to allow liquids to rapidly pass through the envelope web 50. Similar layered absorbent members (laminates) are more fully described in U.S. Pat. No. 4,578,068 entitled "Absorbent Laminate Structure" issued to Timothy A. Kramer, Gerald A. Young and Ronald W. Kock on Mar. 25, 1986, which patent is incorporated herein by reference.

Alternatively, the absorbent cores 42 of the present invention may consist solely of one or more (a multiplicity of the) porous, absorbent, polymeric macrostructures of the present invention; may comprise a combination of layers including the macrostructures of the present invention; or any other absorbent core configurations including one or more of the macrostructures of the present invention.

Figure 10:
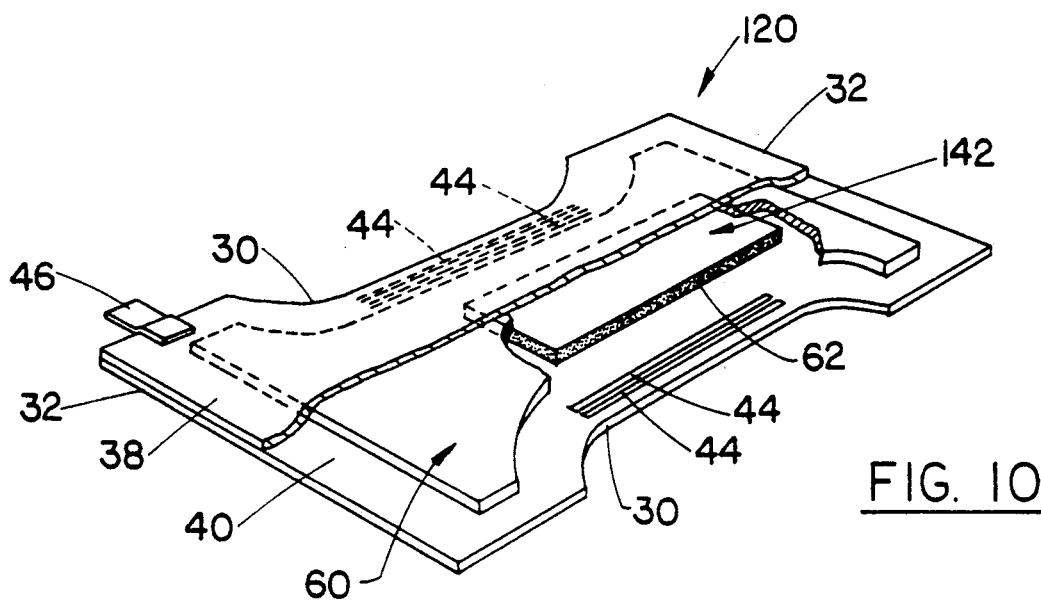
FIG. 10 is a perspective view of a disposable diaper embodiment of the present invention wherein portions of the topsheet have been cut away to more clearly show an alternative absorbent core embodiment.

FIG. 10 shows an alternative embodiment of the diaper 120 comprising a dual-layer absorbent core 142 comprising a modified hourglass-shaped absorbent member 60 and a sheet 62 of the porous, absorbent, polymeric macrostructure positioned subjacent the absorbent member 60 (i.e., between the absorbent member 60 and the backsheet 40).

The absorbent member 60 serves to quickly collect and temporarily hold discharged liquids and to transport such liquids by wicking from the point of initial contact to other parts of the absorbent member 60 and to the macrostructure sheet 62. The absorbent member 60 preferably comprises a web or batt of fiber materials. Various types of fiber material can be used in the absorbent member 60 such as the fiber materials previously discussed herein. Cellulosic fibers are generally preferred for use herein, wood pulp fibers being especially preferred. The absorbent member 60 can also contain specific amounts of a particulate, absorbent, polymeric composition. The absorbent member 60, for example, can contain up to about 50% by its weight of the polymeric composition. In the most preferred embodiments, the absorbent member 60 contains from 0% to about 8% by its weight of a particulate, absorbent, polymeric composition. In alternatively preferred embodiments, the absorbent member 60 comprises chemically stiffened cellulosic fibers as previously discussed herein. Exemplary embodiments of the absorbent member 60 useful in the present invention are described in U.S. Pat. No. 4,673,402 entitled "Absorbent Article With Dual-Layered Cores" which issued to Paul T. Weisman, Dawn I. Houghton, and Dale A. Gellert on Jun. 16, 1987; and U.S. Pat. No. 4,834,735 entitled "High Density Absorbent Members Having Lower Density and Lower Basis Weight Acquisition Zones" issued to Miguel Alemany and Charles J. Berg on May 30, 1989. These patents are hereby incorporated herein by reference. Absorbent members having a storage zone and an acquisition zone having a lower average density and a lower average basis weight per unit area than the storage zone so that the acquisition zone may effectively and efficiently rapidly acquire discharged liquid are especially preferred for use herein.

The absorbent member 60 can be of any desired shape, for example, rectangular, oval, oblong, asymmetric or hourglass-shaped. The shape of the absorbent member 60 may define the general shape of the resulting diaper 120. In the preferred embodiments as shown in FIG. 10, the absorbent member 60 is hourglass-shaped.

The macrostructure sheet 62 of the present invention need not be the same size as the absorbent member 60 and can, in fact, have a top surface which is substantially smaller or larger than the top surface area of the absorbent member 60. As shown in FIG. 10, the macrostructure sheet 62 is smaller than the absorbent member 60 and has a top surface area from about 0.10 to about 1.0 times that of the absorbent member 60. Most preferably, the top surface area of the macrostructure sheet 62 will be only from about 0.10 to about 0.75, and most preferably from about 0.10 to about 0.5 times that of the absorbent member 60. In an alternative embodiment, the absorbent member 60 is smaller than the macrostructure sheet 62 and has a top surface area from about 0.25 to about 1.0 times, more preferably from about 0.3 to about 0.95 times that of the macrostructure sheet 62. In this alternative embodiment, the absorbent member 60 preferably comprises chemically stiffened cellulosic fibers.

The macrostructure sheet 62 is preferably placed in a specific positional relationship with respect to the backsheet 40 and/or the absorbent member 60 in the diaper. More particularly, the macrostructure sheet 62 is positioned generally toward the front of the diaper so that the macrostructure sheet 62 is most effectively located to acquire and hold discharged liquids.

In alternatively preferred embodiments, a multiplicity of macrostructures, preferably from about two to about six macrostructure strips or sheets, may be substituted for the single macrostructure sheet 62 shown in FIG. 10. Further, additional absorbent layers, members, or structures may be placed into the absorbent core 142. For example, an additional absorbent member may be positioned between the macrostructure sheet 62 and the backsheet 40 to provide reserve capacity for the absorbent core 142 and/or a layer to distribute liquids passing through the macrostructure sheet 62 to other portions of the absorbent core 142 or to the macrostructure sheet 62. The macrostructure sheet 62 may also alternatively be positioned over the absorbent member 60 so as to be positioned between the topsheet 38 and the absorbent member 60.

In use, the diaper 20 is applied to a wearer by positioning the back waistband region under the wearer's back, and drawing the reminder of the diaper 20 between the wearer's legs so that the front waistband region is positioned across the front of the wearer. The tape-tab fasteners 46 are then secured preferably to outwardly facing areas of the diaper 20. In use, disposable diapers or other absorbent articles incorporating the porous, absorbent, polymeric macrostructures of the present invention tend to more quickly and efficiently distribute and store liquids and to remain dry due to the high absorbent capacity of the macrostructures.

SYNTHETIC URINE

The specific synthetic urine used in the test methods of the present invention is referred to herein as "Synthetic Urine". The Synthetic Urine is commonly known as Jayco SynUrine and is available from Jayco Pharmaceuticals Company of Camp Hill, Pa. The formula for the Synthetic Urine is: 2.0 g/l of KCl; 2.0 g/l of $Na_2SO_4$; 0.85 g/l of $(NH_4)H_2PO_4$; 0.15 g/l $(NH_4)_2HPO_4$; 0.19 g/l of $CaCl_2$ and 0.23 g/l of $MgCl_2$. All of the chemicals are of reagent grade. The pH of the Synthetic Urine is in the range of 6.0 to 6.4.

TEST METHODS

A. Absorptive Capacity of the Precursor Particles

The polymeric composition is placed within a "tea bag", immersed in an excess of Synthetic Urine for a specified period of time, and then centrifuged for a specific period of time. The ratio of polymeric composition final weight after centrifuging minus initial weight (net fluid gain) to initial weight determines the Absorptive Capacity.

The following procedure is conducted under standard laboratory conditions at 23° C. (73° F.) and 50% relative humidity. Using a 6 cm × 12 cm cutting die, the tea bag material is cut, folded in half lengthwise and sealed along two sides with a T-bar sealer to produce a 6 cm × 6 cm tea bag square. The tea bag material utilized is a grade 1234 heat sealable material, obtainable from C. H. Dexter, Division of the Dexter Corp., Windsor Locks, Conn., U.S.A., or equivalent. Lower porosity tea bag material should be used if required to retain fine particles. 0.200 grams plus or minus 0.005 grams of the polymeric composition is weighed onto a weighing paper and transferred into the tea bag, and the top (open end) of the tea bag is sealed. An empty tea bag is sealed at the top and is used as a blank. Approximately 300 milliliters of Synthetic Urine are poured into a 1,000 milliliter beaker. The blank tea bag is submerged in the Synthetic Urine. The tea bag containing the polymeric composition (the sample tea bag) is held horizontally to distribute the material evenly throughout the tea bag. The tea bag is laid on the surface of the Synthetic Urine. The tea bag is allowed to wet, for a period of no more than one minute, and then is fully submerged and soaked for 60 minutes. Approximately 2 minutes after the first sample is submerged, a second set of tea bags, prepared identically to the first set of blank and sample tea bags, is submerged and soaked for 60 minutes in the same manner as the first set. After the prescribed soak time is elapsed, for each set of tea bag samples, the tea bags are promptly removed (using tongs) from the Synthetic Urine. The samples are then centrifuged as described below. The centrifuge used is a Delux Dynac II Centrifuge, Fisher Model No. 05-100-26, obtainable from Fisher Scientific Co. of Pittsburgh, Pa., or equivalent. The centrifuge should be equipped with a direct read tachometer and an electric brake. The centrifuge is further equipped with a cylindrical insert basket having an approximately 2.5 inch (6.35 cm) high outer wall with an 8.435 inch (21.425 cm) outer diameter, a 7.935 inch (20.155 cm) inside diameter, and 9 rows each of approximately 106 3/32 inch (0.238 cm) diameter circular holes equally spaced around the circumference of the outer wall, and having a basket floor with six ¼ inch (0.635 cm) diameter circular drainage holes equally spaced around the circumference of the basket floor at a distance of ½ inch (1.27 cm) from the interior surface of the outer wall to the center of the drainage holes, or an equivalent. The basket is mounted in the centrifuge so as to rotate, as well as brake, in unison with the centrifuge. The sample tea bags are positioned in the centrifuge basket with a folded end of the tea bag in the direction of the centrifuge spin to absorb the initial force. The blank tea bags are placed to either side of the corresponding sample tea bags. The sample tea bag of the second set must be placed opposite the sample tea bag of the first set; and the blank tea bag of the second set opposite the blank tea bag of the first set, to balance the centrifuge. The centrifuge is started and allowed to ramp up quickly to a stable speed of 1,500 rpm. Once the centrifuge has been stabilized at 1,500 rpm, a timer is set for 3 minutes. After 3 minutes, the centrifuge is turned off and the brake is applied. The first sample tea bag and the first blank tea bag are removed and weighed separately. The procedure is repeated for the second sample tea bag and the second blank tea bag. The Absorptive Capacity (ac) for each of the samples is calculated as follows: ac=(sample tea bag weight after centrifuge minus blank tea bag weight after centrifuge minus dry polymeric composition weight) divided by (dry polymeric composition weight). The Absorptive Capacity value for use herein is the average Absorptive Capacity of the two samples.

B. Fluid Stability

The objective of this method is to determine the stability of an aggregate upon exposure to Synthetic Urine.

The sample macrostructure is placed in a shallow dish. An excess amount of Synthetic Urine is added to the macrostructure. The swelling of the macrostructure is observed until equilibrium is reached. During the observation of the swelling macrostructure, the macrostructure is observed for small particles breaking off from the main aggregate, platelet-like particles floating away from the main aggregate, or particle expansion only in the two dimensional x-y plane with particles breaking and floating away from the main aggregate. If the aggregate has a large number of broken away component particles, the macrostructure is considered unstable. The macrostructure should also be observed for isotropic swelling. If the aggregate remains relatively stable and the relative geometry and spatial relationships of the precursor particles and the pores are maintained after the test procedure, the macrostructure is considered stable. Preferably, fluid stable macrostructures are capable of being picked up in their swollen state without breaking apart.

C. Precursor Particle Size and Mass Average Particle Size

The particle size distribution on a weight percent basis of a 10 gram bulk sample of the precursor particles is determined by sieving the sample through a set of 19 sieves ranging in size from a standard #20 sieve (850 microns) through a standard #400 sieve (38 microns). The sieves are standard sieves as obtainable from the Gilson Company, Inc. of Worthington, Ohio. The procedure is carried out on three stacks of sieves at a time since the equipment used cannot hold all 19 sieves at one time. A first stack contains sieves #20, 25, 30, 35, 40, 45, and 50 plus the sieve pan; the second stack contains sieves #60, 70, 80, 100, 120, and 140 plus the sieve pan; the third stack contains sieves # 170, 200, 230, 270, 325, and 400 plus the sieve pan. The precursor particles remaining on each of these sieves are then weighed to determine the particle size distribution on a weight percent basis.

The first stack of sieves is mounted on a shaker and 10.0 grams plus or minus 0.00 grams of the sample is placed on the #20 sieve. The shaker used is a Vibratory 3-inch Sieve Shaker Model SS-5 as obtainable from the Gilson Company, Inc. of Worthington, Ohio. The stack is shaken for 3 minutes at approximately 2100 vibrations per minute ("6" on the instrument dial). The sieve pan is then removed and the stack set aside for later weighing. Using a soft brush, the sample remaining on the sieve pan is transferred onto a weighing paper. The second stack of sieves is mounted on the shaker and the sample on the weighing paper is transferred onto the #60 sieve. The second stack is shaken for 3 minutes at approximately 2100 vibrations per minute, the sample remaining on the sieve pan being transferred to a weighing paper and the stack set aside. The third stack of sieves is mounted on the shaker and the sample on the weighing paper is transferred onto the #170 sieve. The third stack is shaken for 3 minutes at approximately 2100 vibrations per minute. A soft brush is used to transfer the contents of each given sieve onto a tared weighing paper. The sample is weighed on a standard three place scale and the weight of the sample on the specific sieve is recorded. This step is repeated, using a fresh weighing paper for each sample, for each sieve, and for the sample remaining on the sieve pan after the third stack of sieves has been shaken. The method is repeated for two additional 10 gram samples. The average of the weights of the three samples for each sieve determine the average particle size distribution on a weight percent basis for each sieve size.

The Mass Average Particle Size of the 10 gram bulk sample is calculated as follows:

$$maps = \frac{\Sigma(D_i \times M_i)}{\Sigma M_i}$$

wherein maps is the mass average particle size; $M_i$ is the weight of the particles on the specific sieve; and $D_i$ is the "size parameter" for the specific sieve. The size parameter, $D_i$ of a sieve is defined to mean the size (in microns) of the next highest sieve. For example, a standard #50 sieve has a size parameter of 355 microns, which corresponds to the size of the openings in a standard #45 sieve (the next highest sieve). The Mass Average Particle Size for use herein is the average of the mass average particle size of the three samples.

PRECURSOR PARTICLE EXAMPLE

A jacketed 10 liter twin arm stainless steel kneader measuring 220 mm ×240 mm in the opening and 240 mm in depth, and having two Sigma type blades possessing a rotational diameter of 120 mm is sealed with a lid. An aqueous monomer solution is prepared consisting of 37 weight % monomer. The monomer consists of 75 mole % sodium acrylate and 25 mole % acrylic acid. 5500 grams of the aqueous monomer solution is charged to the kneader vessel, which is subsequently purged with nitrogen gas to remove the remaining entrapped air. Then, the two Sigma type blades are set rotating at rates of 46 rpm and the jacket is heated by the passage of 35° C. water. 2.8 g of sodium persulfate and 0.14 g of L-ascorbic acid are added as polymerization initiators. Polymerization begins about four minutes after the addition of the initiators. A peak temperature of 82° C. is reached inside the reaction system 15 minutes after the addition of the initiators. The hydrated gel polymer is divided into particles about 5 mm in size as the stirring is continued. The lid is removed from the kneader 60 minutes after the start of the polymerization and the material is removed from the kneader.

The resultant hydrated aqueous gel polymer thus obtained is spread on a standard #50 size metal gauze and dried with hot air at 150° C. for 90 minutes. The dried particles are pulverized with a hammer type crusher and sifted with a standard #20 sieve (850 microns) to obtain particles that pass through the standard #20 sieve. The mass average particle size of these particles is 405 microns.

EXAMPLE 1

350.0 grams of precursor particles made in accordance with the Precursor Particle Example are placed into a 5 quart standing kitchen-type mixer. The precursor particles have a particle size such that the precursor particles pass through a standard #60 sieve (250 microns) and are retained on a standard #100 sieve (150 microns). A solution is prepared consisting of 7.0 grams of glycerol, 35.0 grams of methanol, and 7.0 grams of water. This solution is applied to the precursor particles by spraying the solution onto the precursor particles with a Preval Sprayer available from The Precision Valve Corporation of Yonkers, N.Y. The solution is sprayed onto the precursor particles while the mixer is operating. For the first fifteen seconds of spraying, the mixer is run on its lowest speed setting. After the first fifteen seconds, the mixer is run on its highest setting. The total spraying operation requires 3 minutes of elapsed time to spray the entire volume of the solution onto the precursor particles. The mixture is mixed for an additional two minutes at the highest speed setting of the mixer so that all of the precursor particles are thoroughly wetted by the solution. The resultant mixture is then placed into the hopper of an extrusion/compaction unit such as previously described. The extruder screw has a length of 8 inches (20.3 cm) and contains 5 flights, each flight being 1.5 inches (3.8 cm) in length. The outside diameter of the extruder screw is 1.75 inches (4.45 cm) and the screw-to-housing clearance is 0.20 inches (0.51 cm). The unit is activated such that the extruder screw turns at a rate of 47 rpm. The mixture is extruded between two coated steel compaction rolls (nip rolls) with a fixed (but variable) gap. The compaction rolls have a diameter of 8.975 inches (22.8 cm) and are driven at a rate of 5.4 rpm. The gap between the compaction rolls is 0.015 inches (0.38 mm). The formed aggregate sheets are then separated into approximately 12 to 15 inch (30 to 40 cm) lengths. The resultant aggregate sheets are heated in a forced air convection oven at 210° C. for 45 minutes to react the glycerol with the polymer material of the precursor particles. The resultant sheets have a thickness (caliper) of about 0.031 inches (0.8 mm) and a width of about 1.95 inches (4.95 cm).

EXAMPLE 2

A solution is prepared consisting of 0.5 grams of glycerol, 0.5 grams of water, and 3.0 grams of isopropanol. This solution is applied to 25 grams of precursor particles made in accordance with the Precursor Particle Example. The precursor particles have a particle size such that the precursor particles pass through a standard #40 sieve (425 microns) and are retained on a standard #50 sieve (300 microns). The mixture is thoroughly mixed with a stirring spatula until all of the precursor particles are coated with the above solution. The mixture is separated into approximately equal portions. One half of the mixture is spread evenly on a SUPERSTONE baking stone as is available from Sassafras Enterprises Inc. of Evanston, Ill. The mixture is lightly compressed on the stone. 0.16 grams of KODEL polyester fibers are spread evenly onto the formed mixture. The polyester fibers are 1.25 inch (3.2 cm) staple cut length, crimped, 15.0 denier fibers. The second half of the initial mixture is spread evenly on top of the fibers and lightly compressed. This entire structure is then rolled with a wooden rolling pin to a thickness of about 0.06 inches (1.5 mm). A sheet of MYLAR is placed on top of the sheet for rolling in order to prevent the mixture from adhering to the rolling pin. The edges of the sheet are then folded in on themselves and the rolling process is repeated. This folding/rolling (kneading) procedure is performed twice. The sheet is then heated in a forced air circulating oven at 200° C. for 45 minutes to react the glycerol with the polymer material of the precursor particles. The resultant macrostructure has a thickness (caliper) of about 0.06 inches (1.5 mm).

EXAMPLE 3

A solution is prepared consisting of 1.6 grams of glycerol, 3.2 grams of water, and 12.8 grams of isopropanol. This solution is applied to 80 grams of the precursor particles made in accordance with the Precursor Particle Example. The precursor particles have a particle size distribution such that 8% by weight pass through a standard #20 sieve (850 microns) and are retained on a standard #30 sieve (600 microns); 15% by weight pass through a standard #30 sieve (600 microns) and are retained on a standard #40 sieve (425 microns); 22% by weight pass through a standard #40 sieve (425 microns) and are retained on a standard #50 sieve (300 microns); 36% by weight pass through a standard #50 sieve (300 microns) and are retained on a standard #100 sieve (150 microns); and 19% by weight pass through a standard #100 sieve (150 microns). This solution is thoroughly mixed using a stirring spatula until all of the precursor particles are coated with the above solution. The resultant mixture is then spread loosely on a SUPERSTONE baking stone and rolled into a sheet having a thickness of about 0.06 inches (1.5 mm) using a wooden rolling pin. A sheet of MYLAR is placed on top of the sheet for rolling in order to prevent the mixture from adhering to the rolling pin. The sheet is then heated at 200° C. for 45 minutes in a forced air circulating oven to react the glycerol with the polymer material of the precursor particles. The resultant macrostructure has a thickness (caliper) of about 0.06 inches (1.5 mm).

EXAMPLE 4

A solution is prepared consisting of 0.342 grams of glycerol, 0.136 grams of water, and 1.713 grams of methanol. Separately, 0.512 grams of FIBERSORB fibers available from the Arco Chemical Company and 13.364 grams of precursor particles of a size such that all of the particles pass through a standard #100 sieve (150 microns) and made in accordance with the Precursor Particle Example are mixed together to form a precursor particle mixture. The fibers are hand cut from a tow and range in length from about 0.5 inches (1.25 cm) to about 2.5 inches (6.35 cm). The above solution is added to the precursor particle mixture and thoroughly mixed together with a stirring spatula to form an aggregate mixture. The resultant aggregate mixture is spread out on a six inch (15 cm) PYREX culture dish and compressed with a small spatula to a thickness of about 0.15 inches (3.8 mm). The sheet is then heated at 200° C. for 40 minutes in a forced air circulating oven to react the glycerol with the polymer material of the precursor particles (both the polymers of the FIBERSORB and the particles made in the Precursor Particle Example). The resultant macrostructure has a particulate structure of a combination of relatively small irregular shaped granules and fibers intermixed with the granules.

EXAMPLE 5

A solution is prepared consisting of 0.023 grams of glycerol, 0.014 grams of water, and 0.580 grams of methanol. This solution is added to 0.880 grams of precursor particles consisting of FIBERSORB fibers as available from the Arco Chemical Company. The fibers are hand cut from a tow and range in length from about 0.5 inches (1.25 cm) to about 2.5 inches (6.35 cm). The solution and the precursor particles are thoroughly mixed together with a stirring spatula to form an aggregate mixture. The resultant aggregate mixture is spread out on a six inch (15 cm) PYREX culture dish and compressed with a small spatula to a thickness of about 0.007 inches (0.178 mm). The sheet is then heated at 200° C. for 30 minutes in a forced air circulating oven to react the glycerol with the polymer material of the precursor particles. The resultant macrostructure comprises an interfiber crosslinked aggregate having a structure similar to a nonwoven web.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A porous, absorbent, polymeric macrostructure comprising an interparticle crosslinked aggregate comprising (i) a multiplicity of precursor particles of substantially water-insoluble, absorbent, hydrogel-forming, polymer material and (ii) from 0.01 to 30 parts by weight per 100 parts by weight of the precursor particles of an interparticle crosslinking agent reacted with said polymer material of said precursor particles to form covalent crosslink bonds between said precursor particles; said interparticle crosslinked aggregate having pores between adjacent of said precursor particles, said pores being interconnected by intercommunicating channels thus forming a liquid permeable macrostructure, the circumscribed dry volume of the macrostructure being greater than about 10.0 mm³.

2. The macrostructure of claim 1 wherein said precursor particles have a mass average particle size less than about 600 microns.

3. The macrostructure of claim 1 wherein said precursor particles have a mass average particle size less than about 300 microns.

4. The macrostructure of claim 1 wherein said precursor particles comprise fibers.

5. The macrostructure of claim 1 wherein said interparticle crosslinking agent comprises a monomer that is polymerized to form covalent polymeric crosslink bonds between said precursor particles.

6. The macrostructure of claim 1 wherein said polymer material possesses a carboxyl group and said interparticle covalent crosslinking agent has at least two functional groups per molecule capable of reacting with said carboxyl group of said polymer material of said precursor particles.

7. The macrostructure of claim 6 wherein said interparticle crosslinking agent is mixed with water, an organic solvent, or mixtures thereof.

8. The macrostructure of claim 1 wherein said interparticle crosslinked aggregate is surface crosslinked.

9. The macrostructure of claim 1 additionally comprising reinforcing members embedded in the macrostructure.

10. The macrostructure of claim 1 comprising a sheet having a thickness greater than about 250 microns.

11. A porous, absorbent, polymeric macrostructure comprising an interparticle crosslinked aggregate comprising (i) a multiplicity of substantially dry precursor particles of substantially water-insoluble, absorbent, hydrogel-forming, polymer material, said polymer material of said precursor particles being selected from the group consisting of hydrolyzed starch-acrylonitrile graft copolymer; partially neutralized starch-acrylonitrile graft copolymer; starch-acrylic acid graft copolymer; partially neutralized starch-acrylic acid graft copolymer; saponified vinyl acetate-acrylic ester copolymers; hydrolyzed arylonitcrile or acrylamide copolymers; slightly network crosslinked products of any of the foregoing copolymers; partially neutralized polyacrylic acid; or slightly network crosslinked products of partially neutralized polyacrylic acid; and (ii) an interparticle crosslinking agent reacted with said polymer material of said precursor particles to form crosslink bonds between said precursor particles, said interparticle crosslinking agent being selected from the group consisting of polyhydric alcohol compounds, polyglycidyl ether compounds, polyfunctional aziridine compounds, polyfunctional amine compounds, and polyfunctional isocyanate compounds; said interparticle crosslinked aggregate having pores between adjacent of said precursor particles, said pores being interconnected by intercommunicating channels so that the macrostructure is liquid permeable, the circumscribed dry volume of the macrostructure being greater than about 100.0 mm³.

12. The macrostructure of claim 11 wherein said precursor particles comprise fibers.

13. The macrostructure of claim 11 wherein the mass average particle size of said precursor particles is less than about 500 microns.

14. The macrostructure of claim 11 wherein said precursor particles have a mass average particle size less than about 300 microns.

15. The macrostructure of claim 14 wherein said interparticle crosslinking agent is mixed with water, a hydrophilic organic solvent, or mixtures thereof.

16. The macrostructure of claim 15 wherein said polymer material of said precursor particles consists essentially of slightly network crosslinked products of partially neutralized polyacrylic acid; and said interparticle crosslinking agent is selected from the group consisting of ethylene glycol, glycerol, trimethylol propane, 1,2-propanediol, or 1,3-propanediol.

17. The macrostructure of claim 16 wherein at least about 95% by weight of said precursor particles have a particle size between about 150 microns and about 300 microns.

18. The macrostructure of claim 17 comprising a sheet having a thickness greater than about 250 microns.

19. The macrostructure of claim 16 wherein the mass average particle size of said precursor particles is less than about 180 microns; and at least about 95% by weight of said precursor particles have a particle size between about 90 microns and about 180 microns.

20. The macrostructure of claim 19 comprising a sheet having a thickness greater than about 250 microns.

21. The macrostructure of claim 11, 12, 14, 18, or 20 wherein said interparticle crosslinked aggregate is surface crosslinked.

22. The macrostructure of claim 11, 12, 14, 18, or 20 additionally comprising reinforcing fibers embedded in the macrostructure.

23. The macrostructure of claim 22 wherein said reinforcing fibers comprise synthetic fibers.

24. The macrostructure of claim 11, 12, 14, 16, 18, or 20 comprising a sheet having a thickness between about 0.5 mm and about 3.0 mm.

25. An absorbent product comprising a substrate and the macrostructure according to claim 1, 11, 12, 14, 18, or 20 joined to said substrate.

26. An absorbent article comprising a liquid pervious topsheet; a liquid impervious backsheet joined with said topsheet; and an absorbent core positioned between said topsheet and said backsheet, said absorbent core comprising one or more of the macrostructures of claim 1, 5, 11, 12, 14, 18, or 20.

27. The absorbent article of claim 26 wherein said absorbent core additionally comprises an envelope web encasing said macrostructure.

28. The absorbent article of claim 27 wherein said envelope web comprises a nonwoven web of hydrophilized synthetic fibers that is sealed about its periphery.

29. The absorbent article of claim 26 wherein said absorbent core additionally comprises an absorbent member positioned between said topsheet and said macrostructure.

30. The absorbent article of claim 26 wherein said macrostructure additionally comprises reinforcing fibers embedded in said macrostructure.

* * * * *

UNITED STATES PATENT AND TRADEMARK OFFICE
CERTIFICATE OF CORRECTION

PATENT NO. : 5,124,188

DATED : June 23, 1992

INVENTOR(S) : Donald C. Roe, et al.

It is certified that error appears in the above-indentified patent and that said Letters Patent is hereby corrected as shown below:

Title Page:

Abstract, line 6 "soluble" should read --insoluble--.

Page 2, FOREIGN PATENT DOCUMENTS, right hand column, line 5 "63-023846" should read --88-023846--.

Page 2, FOREIGN PATENT DOCUMENTS, right hand column, line 6 "63-025935" should read --88-025935--.

Page 2, FOREIGN PATENT DOCUMENTS, right hand column, line 7 "64-289790" should read --89-289790--.

Column 24, line 55 "member$" should read --members--.

Column 33, claim 11 should read as follows:

A porous, absorbent, polymeric macrostructure comprising an interparticle crosslinked aggregate comprising (i) a multiplicity of substantially dry precursor particles of substantially water-insoluble, absorbent, hydrogel-forming, polymer material, said polymer material of said precursor particles being selected from the group consisting of hydrolyzed starch-acrylonitrile graft copolymer; partially neutralized starch-acrylonitrile graft copolymer; starch-acrylic acid graft copolymer; partially neutralized starch-acrylic acid graft copolymer; saponified vinyl acetate-acrylic ester copolymers; hydrolyzed acrylonitrile or acrylamide copolymers; slightly network crosslinked products of any of the foregoing copolymers; partially neutralized polyacrylic acid; or slightly network crosslinked products of partially neutralized polyacrylic acid; and (ii) an interparticle crosslinking agent reacted with said polymer material of said precursor particles to form crosslink bonds between said precursor particles; said interparticle crosslinking agent being selected from the group consisting of polyhydric alcohol compounds, polyglycidyl ether compounds, polyfunctional aziridine compounds, polyfunctional amine compounds, and polyfunctional isocyanate compounds; said interparticle crosslinked aggregate having pores between adjacent of said precursor particles, said pores being

UNITED STATES PATENT AND TRADEMARK OFFICE
CERTIFICATE OF CORRECTION

PATENT NO. : 5,124,188
DATED : June 23, 1992
INVENTOR(S) : Donald C. Roe, et al.

It is certified that error appears in the above-indentified patent and that said Letters Patent is hereby corrected as shown below:

interconnected by intercommunicating channels so that the macrostructure is liquid permeable, the circumscribed dry volume of the macrostructure being greater than about $100.0 mm^3$.

Signed and Sealed this

Twenty-sixth Day of September, 1995

Attest:

BRUCE LEHMAN

Attesting Officer

Commissioner of Patents and Trademarks